(12) United States Patent
Douglas et al.

(10) Patent No.: US 11,627,299 B1
(45) Date of Patent: Apr. 11, 2023

(54) METHOD AND APPARATUS FOR A STEREOSCOPIC SMART PHONE

(71) Applicants: Robert Edwin Douglas, Winter Park, FL (US); Kathleen Mary Douglas, Winter Park, FL (US); David Byron Douglas, Winter Park, FL (US)

(72) Inventors: Robert Edwin Douglas, Winter Park, FL (US); Kathleen Mary Douglas, Winter Park, FL (US); David Byron Douglas, Winter Park, FL (US)

(73) Assignee: Opic, Inc., Winter Park, FL (US)

( * ) Notice: Subject to any disclaimer, the term of this patent is extended or adjusted under 35 U.S.C. 154(b) by 0 days.

(21) Appl. No.: 17/829,256

(22) Filed: May 31, 2022

Related U.S. Application Data

(63) Continuation-in-part of application No. 16/997,830, filed on Aug. 19, 2020, which is a continuation-in-part of application No. 16/936,293, filed on Jul. 22, 2020, application No. 17/829,256, which is a continuation-in-part of application No. 17/558,606, filed on Dec. 22, 2021, which is a continuation-in-part of application No. 17/225,610, filed on Apr. 8, 2021, now Pat. No. 11,366,319.

(60) Provisional application No. 62/889,169, filed on Aug. 20, 2019.

(51) Int. Cl.
| | |
|---|---|
| H04N 13/239 | (2018.01) |
| H04N 13/344 | (2018.01) |
| H04N 13/296 | (2018.01) |
| H04N 13/194 | (2018.01) |
| H04N 23/69 | (2023.01) |
| H04N 23/695 | (2023.01) |
| H04M 1/02 | (2006.01) |
| G06V 20/20 | (2022.01) |
| G06F 3/01 | (2006.01) |

(52) U.S. Cl.
CPC ......... *H04N 13/239* (2018.05); *H04N 13/194* (2018.05); *H04N 13/296* (2018.05); *H04N 13/344* (2018.05); *H04N 23/69* (2023.01); *H04N 23/695* (2023.01); *G06F 3/013* (2013.01); *G06V 20/20* (2022.01); *H04M 1/0264* (2013.01)

(58) Field of Classification Search
CPC ......... H04N 2013/0081; H04N 13/204; H04N 13/00; G06T 7/593; G06T 2207/10012
See application file for complete search history.

(56) References Cited

U.S. PATENT DOCUMENTS

| | | | |
|---|---|---|---|
| 2015/0116202 A1* | 4/2015 | Kuroki | H04N 13/106 345/156 |
| 2016/0086379 A1* | 3/2016 | Sadi | G02B 27/0093 345/633 |
| 2020/0349846 A1* | 11/2020 | Siboni | H04N 13/239 |

* cited by examiner

*Primary Examiner* — Ross Varndell

(57) ABSTRACT

This patent provides a novel stereoscopic imaging system. In the preferred embodiment, the improved stereoscopic imaging system would be incorporated onto a smart phone, which is called the stereoscopic smart phone (SSP). The SSP would work in conjunction with one or more stereoscopic head display units (SHDUs). Once this system is operational, it will allow significant improvements to obtaining stereoscopic imagery. One novel aspect of this patent comprises wherein the stereoscopic cameras on the SSP can move in position to alter stereo separation distance and change the convergence to optimally image a scene.

20 Claims, 18 Drawing Sheets

SMART PHONE WITH STEREOSCOPIC CAMERA CAPABILITY
Fig. 1A Back of Smart Phone
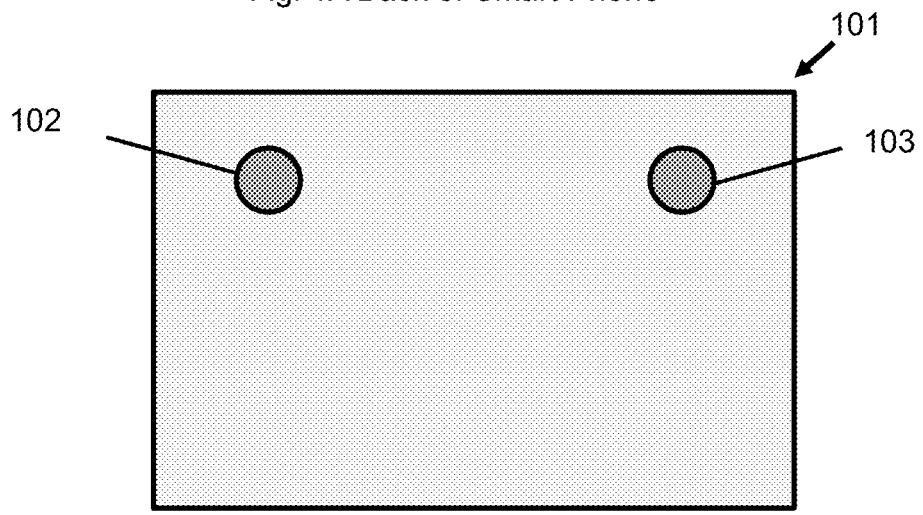
Fig. 1B Front of Smart Phone
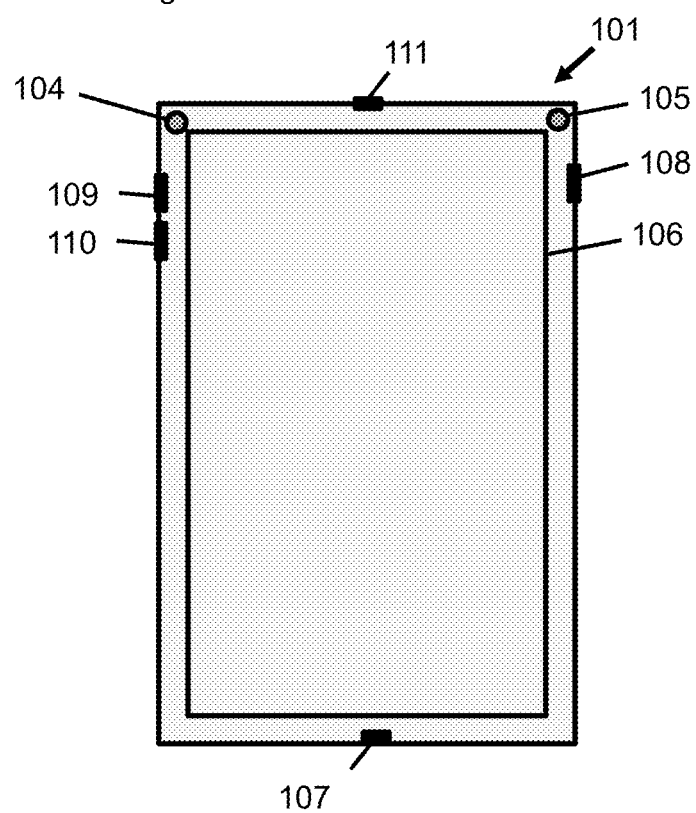

KEY COMPONENTS OF SMART PHONE WITH STEREOSCOPIC
CAMERA CAPABILITY

Fig. 2A Key Components

| Stereoscopic Camera Components |
|---|
| • Aperture<br>• Lens: curved; fish eye; progressive<br>• Camera cluster<br>• Shutter<br>• Eye tracking Sensor array<br>• Processor<br>• Software<br>• Mirror (optional)<br>• Mechanical devices (optional)<br>• Display<br>• Communications links<br><div align="center">200</div> |

ILLUSTRATION OF CONVERGENCE OF STEREOSCOPIC CAMERAS
ON A SMART PHONE
Fig. 2B Top down view of SSP
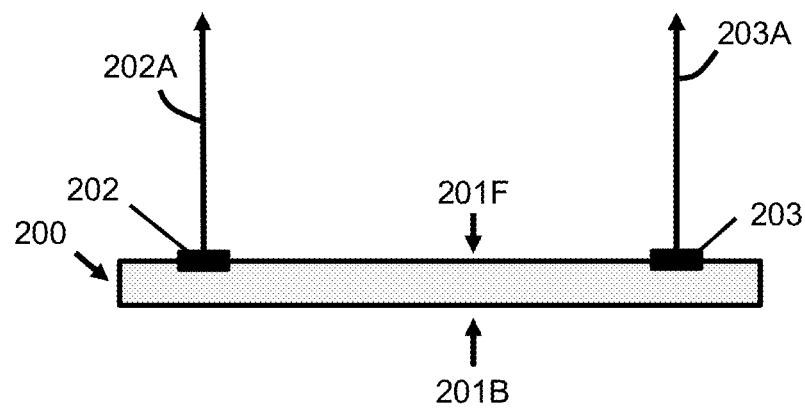
Fig. 2C Top down illustrating convergence of SSP
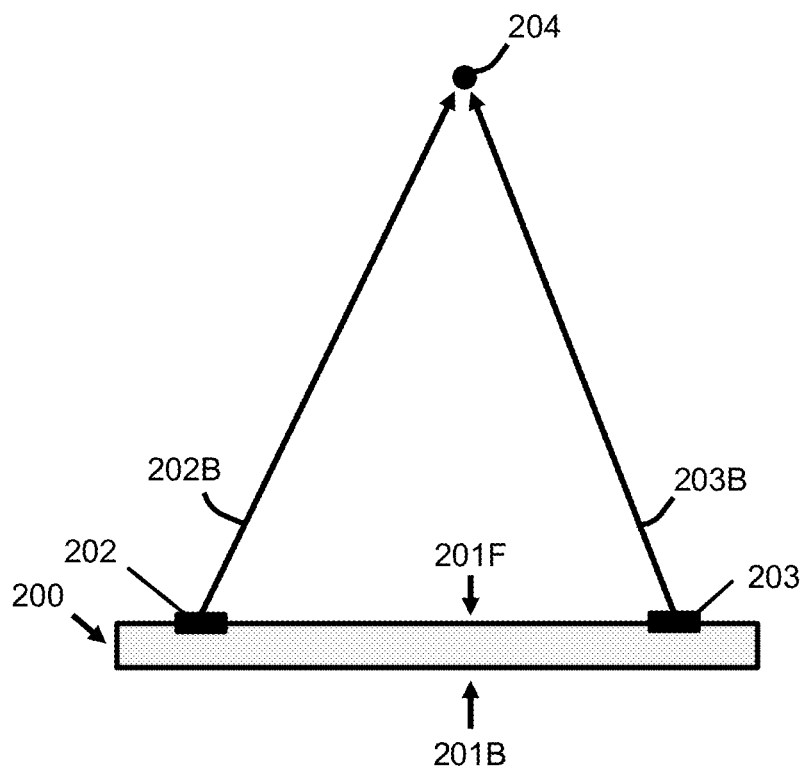

ALTERNATIVE LENS CONCEPTS FOR SMART PHONE WITH
STEREOSCOPIC CAMERA CAPABILITY
Fig. 3A Curved lens concept
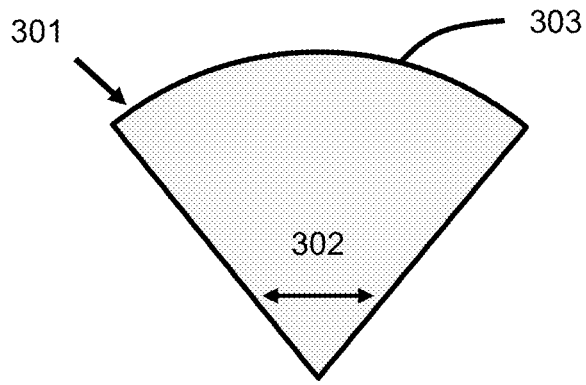
Fig. 3B Fish eye type of lens concept
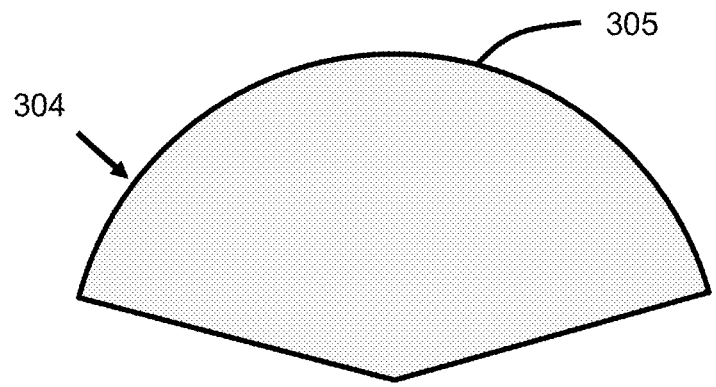
Fig. 3C Progressive type of lens concept
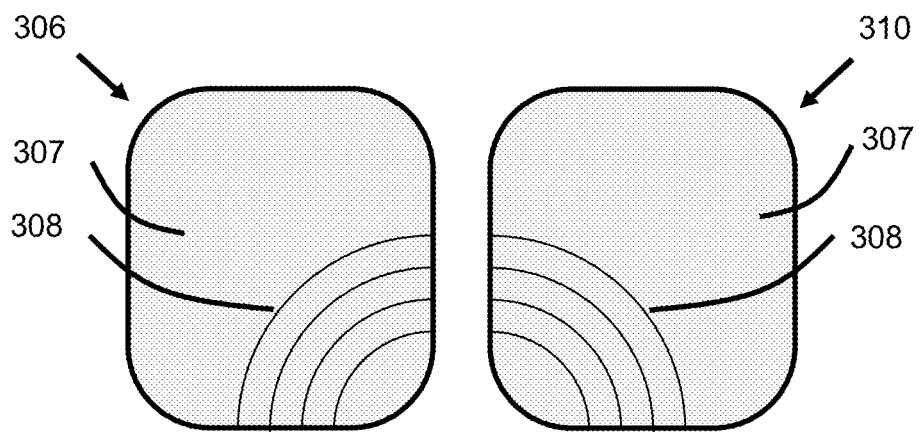

COMPOSITE SENSOR ARRAY CONCEPT FOR SMART PHONE
WITH STEREOSCOPIC CAMERA CAPABILITY
Fig. 4A Front View of Composite Sensor Array
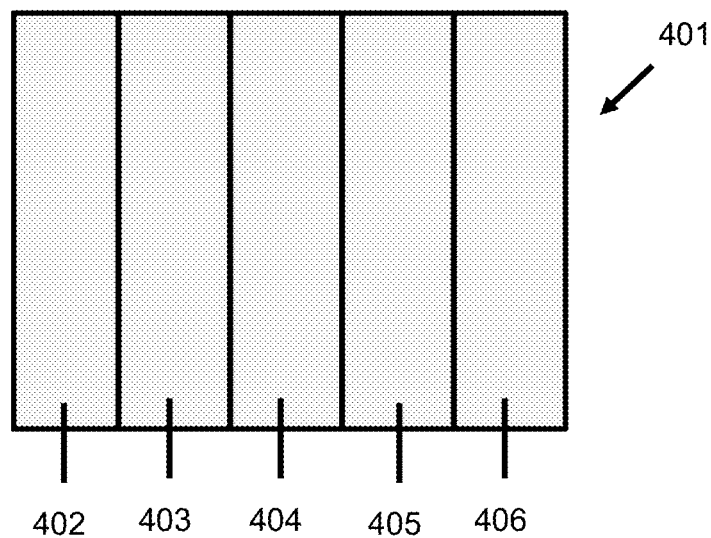
Fig. 4B Top View of Composite Sensor Array
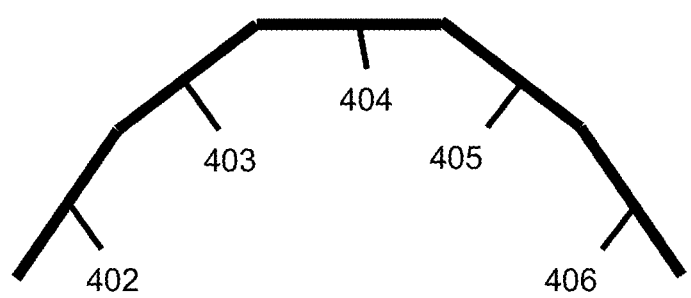

MIRROR CONCEPTS FOR SMART PHONE WITH
STEREOSCOPIC CAMERA CAPABILITY
Fig. 5A Front view of flat mirror
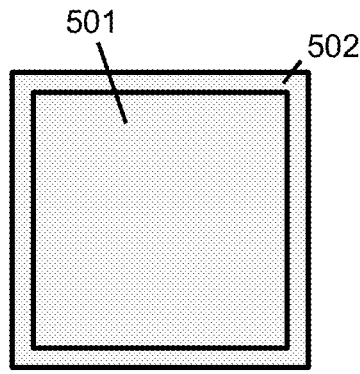
Fig. 5B Top-down view of flat mirror
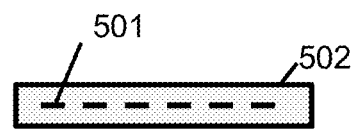
Fig. 5C Front view of curved mirror
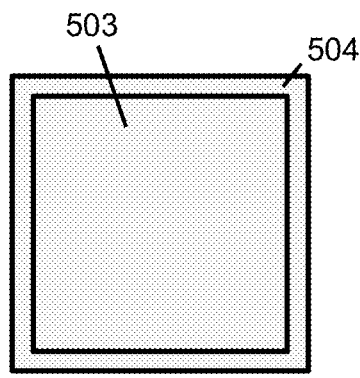
Fig. 5D Top-down view of curved mirror
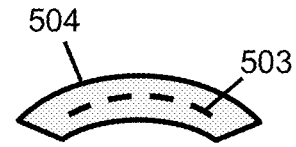
Fig. 5E Front view of deformable mirror
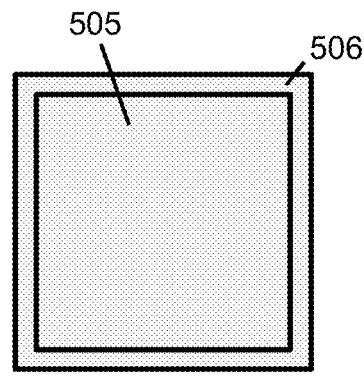
Fig. 5F Top-down view of deformable mirror, t = 1
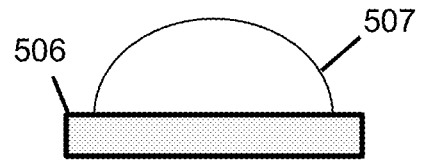
Fig. 5G Top-down view of deformable mirror, t = 2
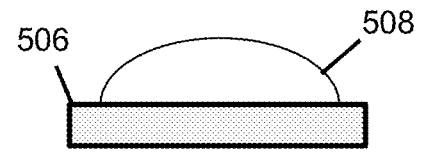

CONCEPTS OF FLEXIBILITY FOR SMART PHONE WITH
STEREOSCOPIC CAMERA CAPABILITY
Fig. 6A Movable lens concept
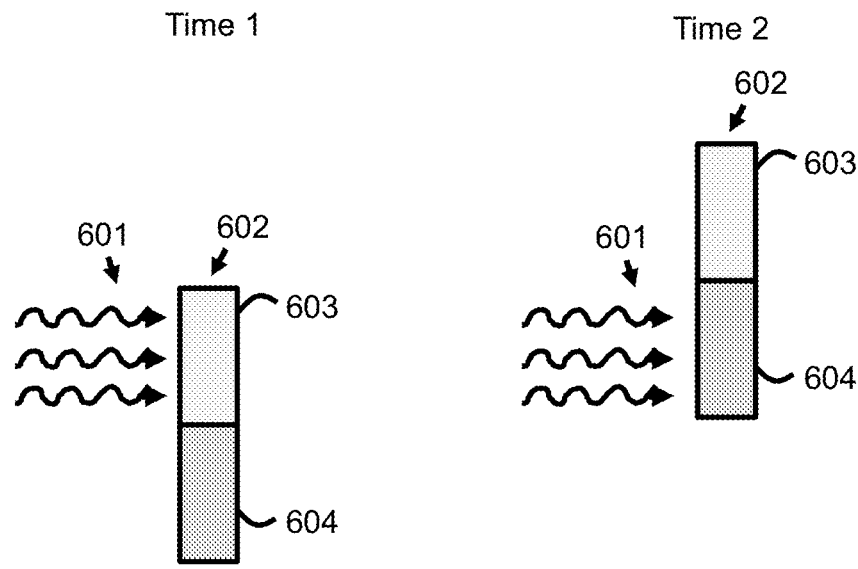
Fig. 6B composite sensor array concept
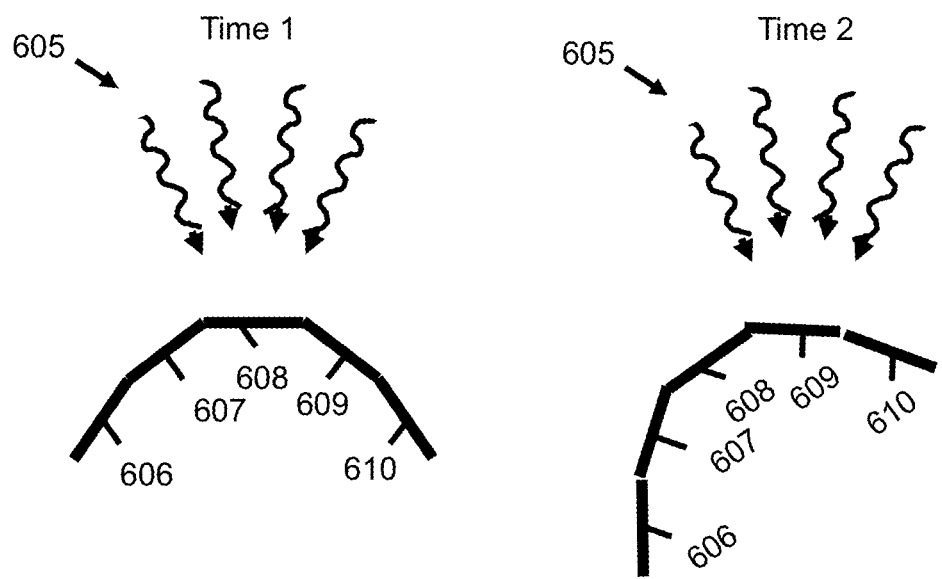

CONCEPTS OF FLEXIBILITY FOR SMART PHONE WITH
STEREOSCOPIC CAMERA CAPABILITY
Fig. 6C Switching out of cameras concept
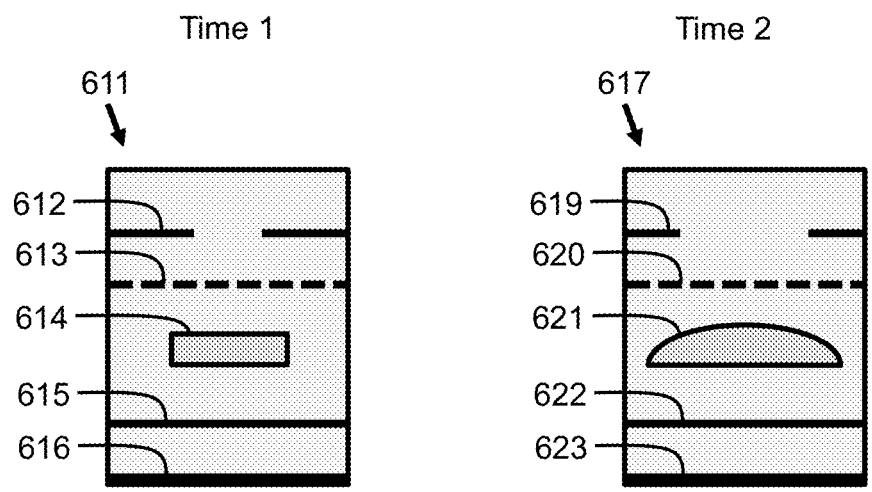

STEREOSCOPIC HEAD DISPLAY UNIT (SHDU)
Fig. 7A SHDU
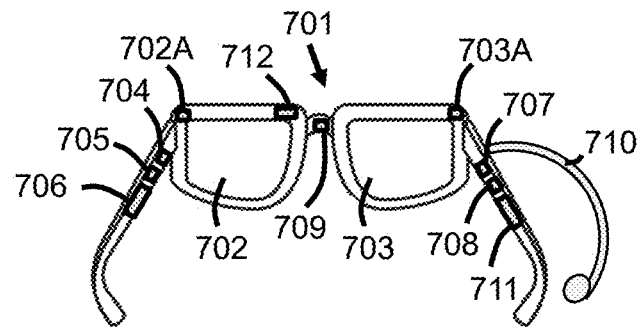
Fig. 7B SHDU Eyepiece Cover
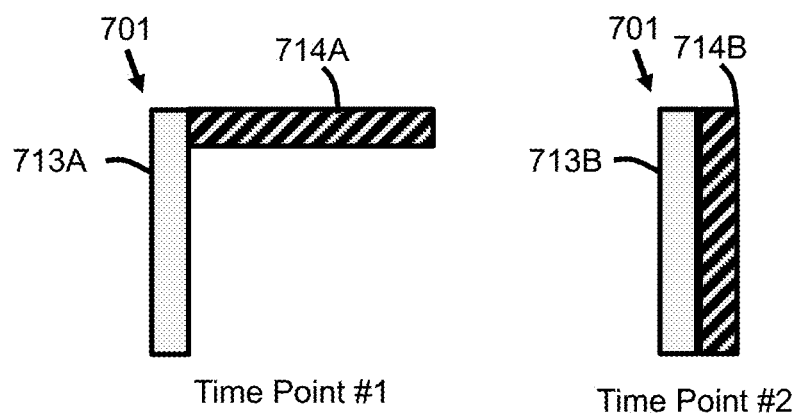
Fig. 7C SHDU Eyepiece Cover
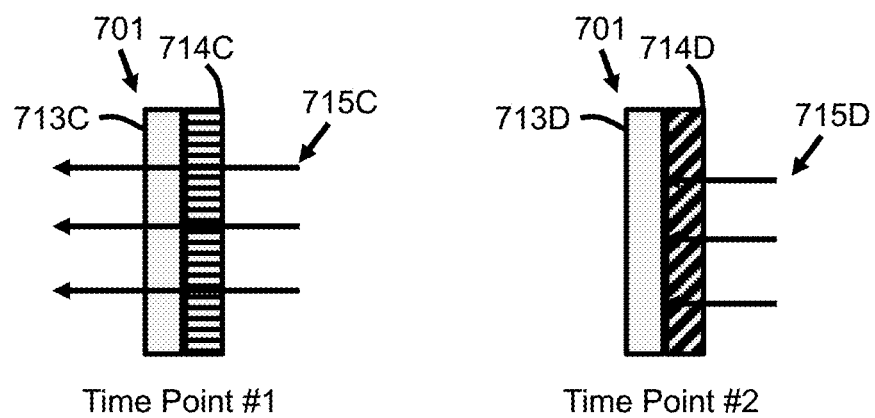

CONNECTIVITY MEANS BETWEEN SMART PHONE WITH STEREOSCOPIC CAMERA CAPABILITY AND STEREOSCOPIC HEAD DISPLAY UNIT
Fig. 8A SSP and SHDU wired connectivity
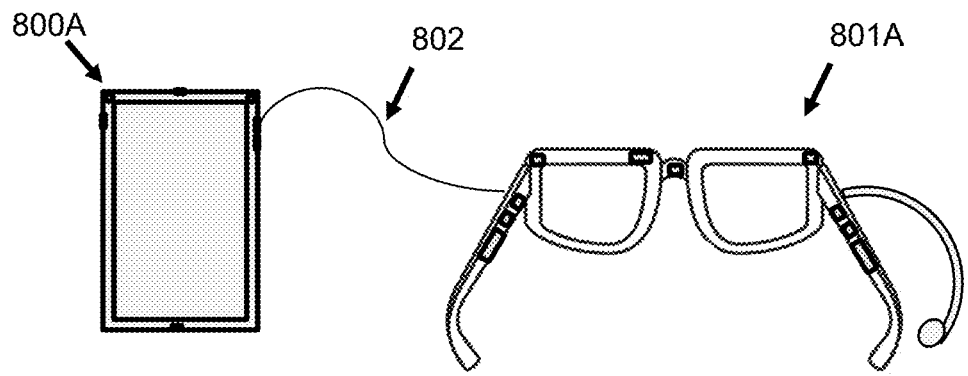
Fig. 8B SSP and SHDU wireless connectivity via BlueTooth
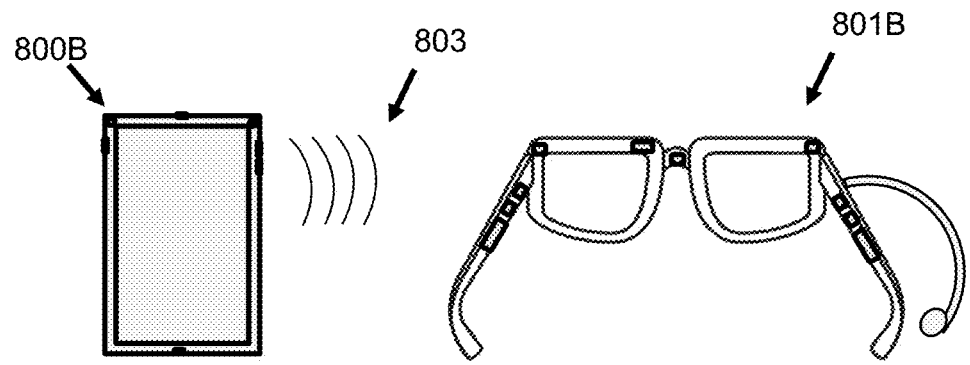
Fig. 8C SSP and SHDU wireless connectivity via Internet
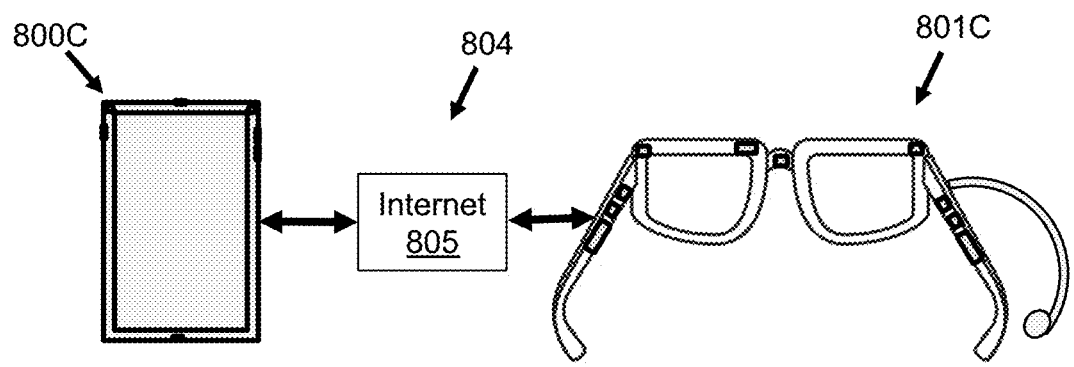

SYSTEM OPERATION USING THE SMART PHONE WITH STEREOSCOPIC CAMERA CAPABILITY
FIG. 9A System operation using the SSP
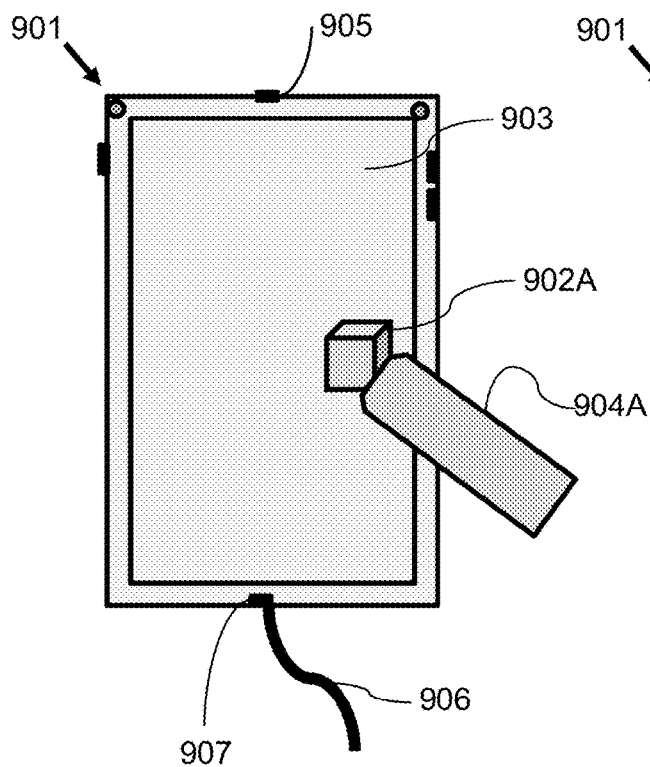
FIG. 9C System operation using the SSP
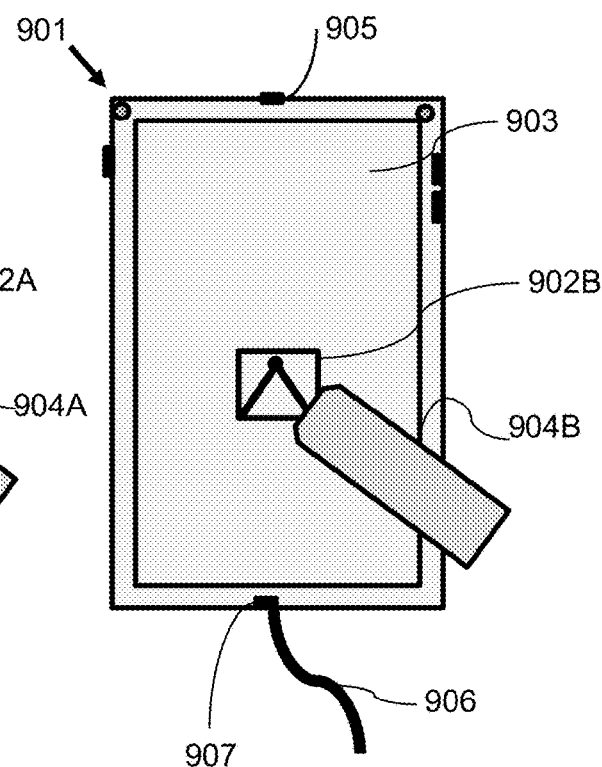
FIG. 9B Near real-time stereo mode, time N
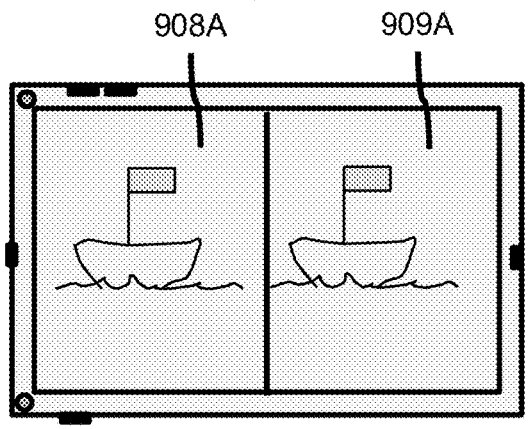
FIG. 9D Near real-time stereo mode, time N +1
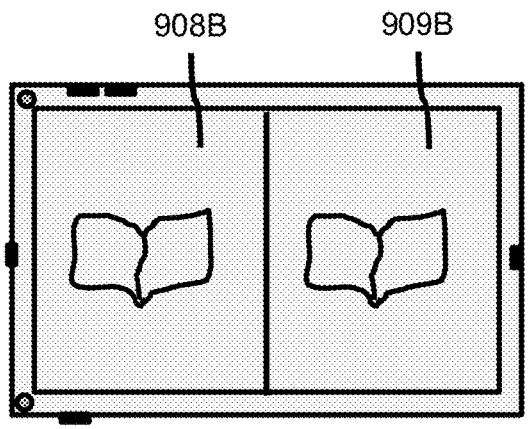

BEFORE AND AFTER APPLICATION OF AUTOMATIC
OBJECT RECOGNITION AS DISPLAYED ON THE SHDU
FIG. 10A System operation using the stereoscopic smart phone (SSP)
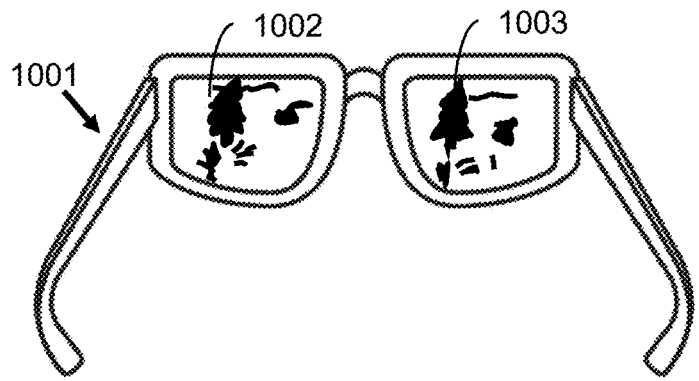
FIG. 10B System operation using the stereoscopic smart phone (SSP)
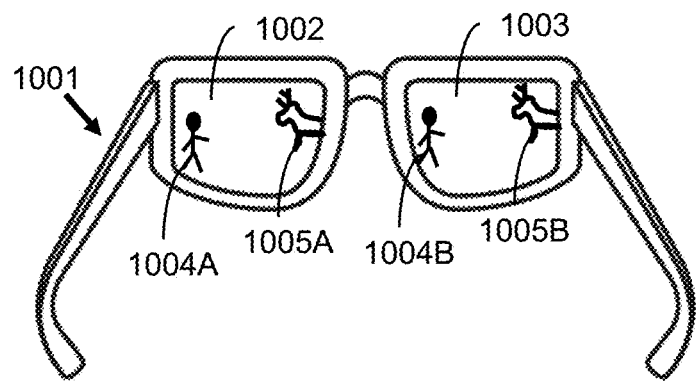
FIG. 10C System operation using the stereoscopic smart phone (SSP)
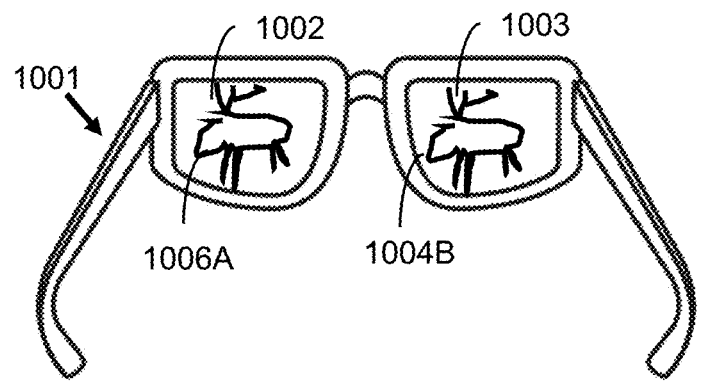

APPLICATION OF ARTIFICIAL INTELLIGENCE IN CONJUNCTION WITH OF AUTOMATIC OBJECT RECOGNITION AS DISPLAYED ON THE SHDU
FIG. 11A Stereoscopic image stabilization
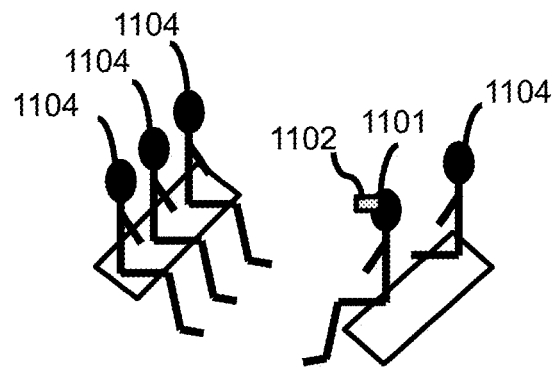
FIG. 11B Stereoscopic image stabilization implemented
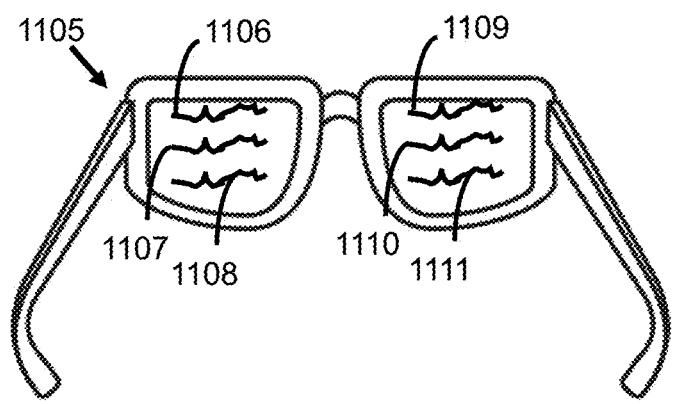

APPLICATION OF ARTIFICIAL INTELLIGENCE IN CONJUNCTION WITH OF AUTOMATIC OBJECT RECOGNITION AS DISPLAYED ON THE SHDU
FIG. 11C Stereoscopic image stabilization
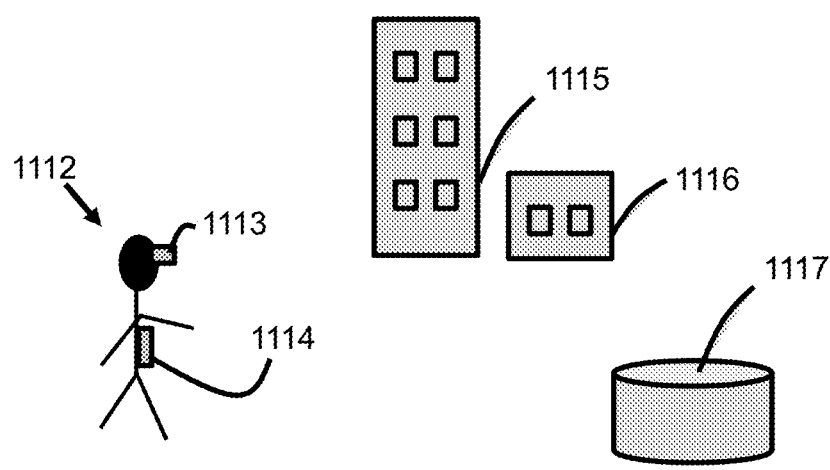
FIG. 11D Stereoscopic image stabilization implemented
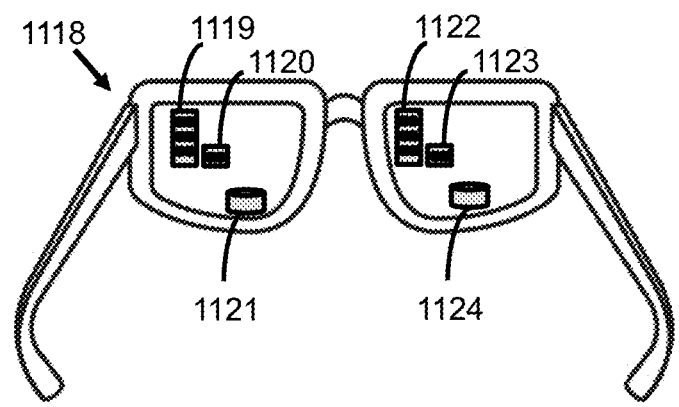

STEREOSCOPIC IMAGE STABILIZATION
FIG. 12A Determining a stabilization point and FOV for the left eye imagery and right eye imagery
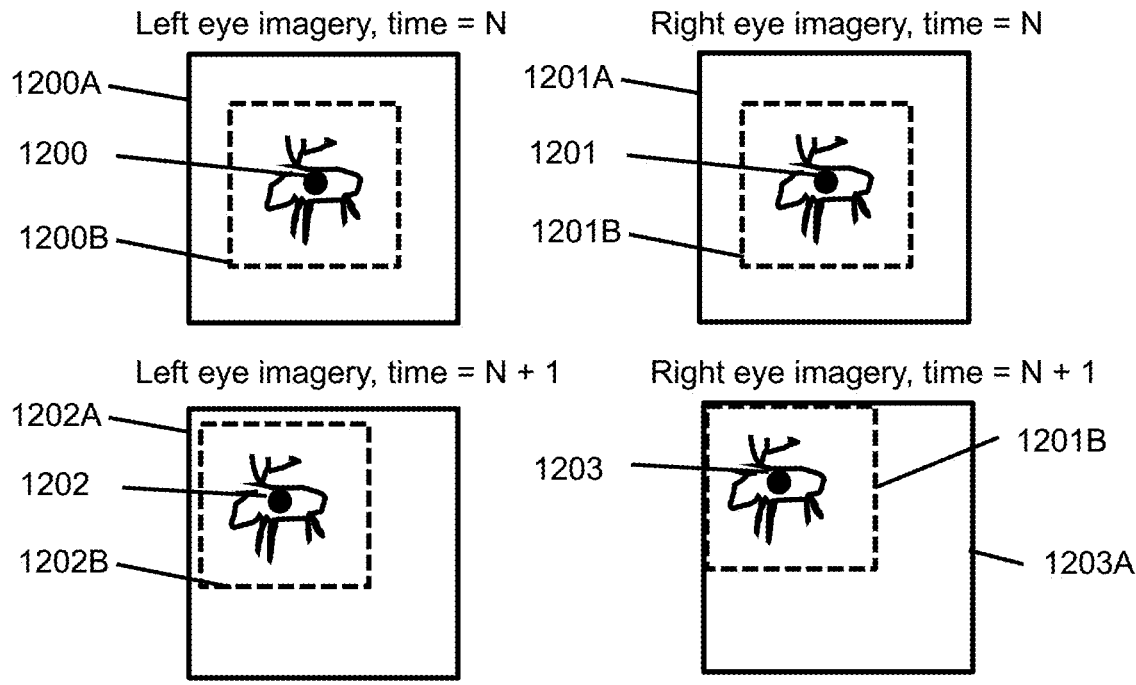
FIG. 12B Displaying stabilized stereoscopic imagery on a SHDU
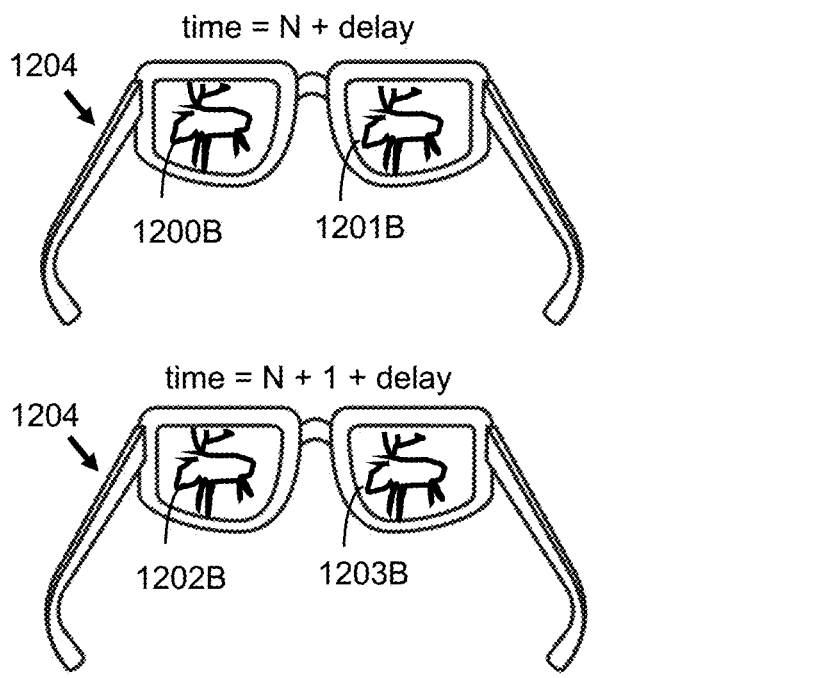

SMART PHONE WITH MOVABLE STEREOSCOPIC CAMERAS
Fig. 13A Back of Smart Phone at t = N
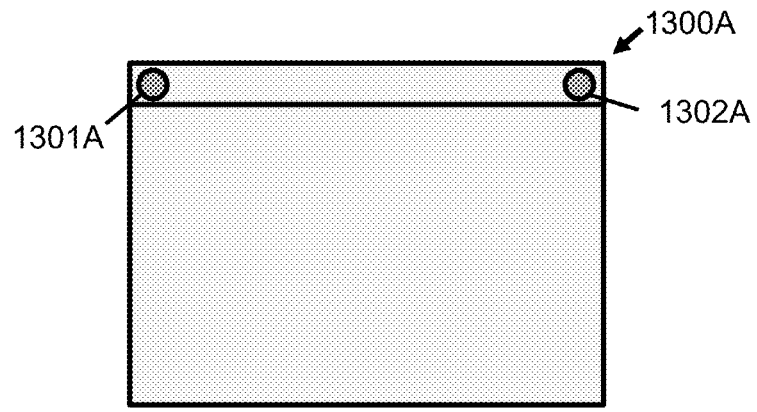
Fig. 13B Back of Smart Phone at t = N + 1
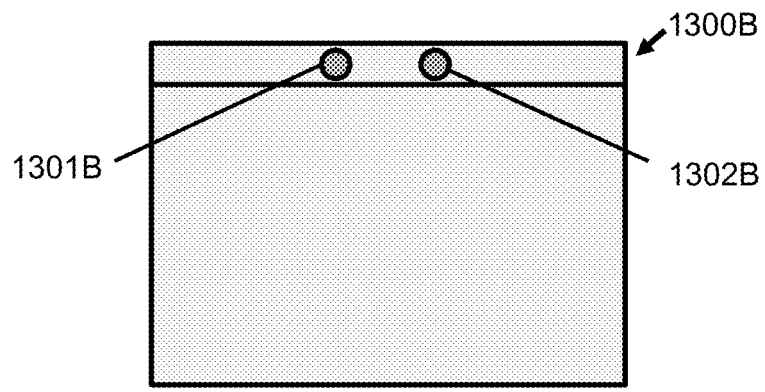
Fig. 13C Back of Smart Phone at t = N + 2
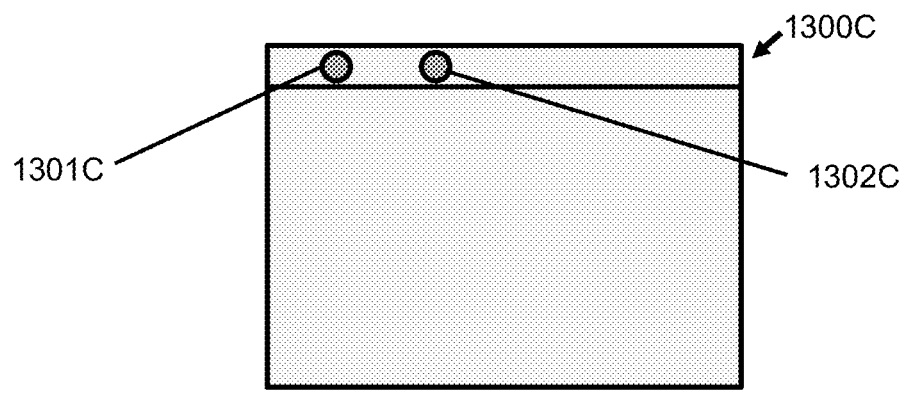

ADJUSTING STEREOSCOPIC CAMERA COMPONENTRY
BASED ON EYE TRACKING PARAMETERS OF A USER

METHOD AND APPARATUS FOR A STEREOSCOPIC SMART PHONE

CROSS-REFERENCES TO RELATED APPLICATIONS

This patent application is a continuation-in-part of U.S. Ser. No. 16/997,830 filed on Aug. 19, 2020, which claims benefit of U.S. Provisional Application 62/889,169 filed on Aug. 20, 2019 and is a continuation-in-part of U.S. Ser. No. 16/936,293 filed on Jul. 22, 2020. This patent application is also a continuation-in-part of U.S. Ser. No. 17/558,606 filed on Dec. 22, 2021, which is a continuation-in-part of U.S. Ser. No. 17/225,610 filed on Apr. 8, 2021. All of these are incorporated by reference in their entirety.

TECHNICAL FIELD

Aspects of this disclosure are generally related to three-dimensional imaging.

BACKGROUND

Many people use smart phones.

SUMMARY

All examples, aspects and features mentioned in this document can be combined in any technically possible way.

This patent provides a novel stereoscopic imaging system. In the preferred embodiment, the improved stereoscopic imaging system would be incorporated onto a smart phone, which is called the stereoscopic smart phone (SSP). The SSP would work in conjunction with one or more stereoscopic head display units (SHDUs). Once this system is operational, it will allow significant improvements to video imagery. For example, the stereoscopic cameras on the SSP can move in position to alter stereo separation distance and change the convergence to optimally image a scene. These changes can occur in near real time, so as the scene changes, the cameras change accordingly. Consider the following situation with a rolly polly bug. A SSP can be set up near the SSP and object tracking of the rolly polly can occur. Each camera of the stereoscopic camera system on the SSP can track the rolly polly and the stereo distance can change closer and farther away based on the distance of the rolly polly. The rolly polly can climb onto a rock and the convergence point of the stereo cameras moves upward and as it climbs downward into a hole, the convergence point of the stereo cameras moves downwards. While all of this is happening, the stereoscopic imagery can be passed via a wired or wireless connection to a stereoscopic head display unit (SHDU). A child in near real time can view the rolly polly while wearing the SHDU. The digital images of the rolly polly can be enlarged so the rolly polly appears the size of a black lab puppy. A wide array of other objects and situations can also be imaged using this system, which overall enhance the viewing experience.

The preferred embodiment is a method of stereoscopic imaging comprising: using a left camera and a right camera of a stereoscopic camera system image to perform initial stereoscopic imaging of an area wherein said left camera has a location on said stereoscopic camera system, wherein said right camera has a location on said stereoscopic camera system, wherein said left camera's location and said right camera's location are separated by a stereoscopic distance, wherein said left camera has first pointing direction, and wherein said right camera has first pointing direction; changing said left camera's first pointing direction to a second pointing direction wherein said left camera's second pointing direction is different than said left camera's first pointing direction, and wherein said left camera's second pointing direction points towards a convergence point; changing said right camera's first pointing direction to a second pointing direction wherein said right camera's second pointing direction is different than said right camera's first pointing direction, and wherein said right camera's second pointing direction points towards said convergence point; and using said left camera and said right camera of said stereoscopic camera system to perform subsequent stereoscopic imaging of said area with said left camera's second pointing direction and said right camera's second pointing direction.

Some embodiments comprise wherein said convergence point is positioned such that a distance from said left camera's location to said convergence point is not equal to a distance from said right camera's location to said convergence point.

Some embodiments comprise wherein said convergence point is positioned such that a distance from said left camera's location to said convergence point is equal to a distance from said right camera's location to said convergence point.

Some embodiments comprise wherein said left camera's first pointing direction points towards a second convergence point and said left camera's second pointing direction points towards said convergence point; and wherein said second convergence point is different from said convergence point.

Some embodiments comprise wherein said initial stereoscopic imaging has a first zoom setting; wherein said subsequent stereoscopic imaging has a second zoom setting; and wherein said second zoom setting has greater magnification than said first zoom setting.

Some embodiments comprise wherein said left camera's first pointing direction is determined based on said left camera's orientation; and wherein said right camera's first pointing direction is determined based on said right camera's orientation.

Some embodiments comprise displaying left eye imagery and right eye imagery from said initial stereoscopic imaging of said area on a stereoscopic head display unit (SHDU); and displaying left eye imagery and right eye imagery from said subsequent stereoscopic imaging of said area on said SHDU wherein said SHDU comprises a virtual reality display, an augmented reality display or a mixed reality display.

Some embodiments comprise wherein said stereoscopic system is used on a smart phone; and wherein said SHDU and said smart phone communicate via a wired connection, a wireless connection via BlueTooth or a wireless connection via an Internet. Some embodiments comprise wherein automatic object recognition is performed on said left eye imagery and said right eye imagery from said initial stereoscopic imaging of said area on said SHDU. Some embodiments comprise wherein artificial intelligence is performed in conjunction with said automatic object recognition to alert a user regarding findings in said area. Some embodiments comprise wherein stereoscopic image stabilization is performed on said left eye imagery and said right eye imagery from said initial stereoscopic imaging of said area on said SHDU. Some embodiments comprise determining a spatial relationship between said stereoscopic camera system and an object of interest; and reconfiguring said stereoscopic cameras based on said spatial relationship wherein reconfiguring said stereoscopic cameras comprises changing said stereoscopic distance to a subsequent stereoscopic distance wherein said subsequent stereoscopic distance is different than said stereoscopic distance.

Some embodiments comprise wherein said subsequent stereoscopic imaging of said area is performed using a second stereoscopic distance; and wherein said second stereoscopic distance is smaller than said first stereoscopic distance.

Some embodiments comprise wherein said stereoscopic camera system is placed on a smart phone, a tablet or a laptop.

Some embodiments comprise wherein said convergence point is determined based on an object's location in said area.

Some embodiments comprise wherein said convergence point is determined based on eye tracking metrics of a user.

Some embodiments comprise wherein said convergence point is determined based on an artificial intelligence algorithm.

Some embodiments comprise wherein a sensor system of said stereoscopic camera system comprises a composite sensor array.

Some embodiments comprise a stereoscopic head display unit (SHDU) comprising: a head display unit with a left eye display and a right eye display wherein said SHDU is configured to: receive initial stereoscopic imagery from a stereoscopic imaging system wherein said initial stereoscopic imagery comprises initial left eye imagery and initial right eye imagery; display said initial left eye imagery on said left eye display; display said initial right eye imagery on said right eye display; receive subsequent stereoscopic imagery from said stereoscopic imaging system wherein said subsequent stereoscopic imagery comprises subsequent left eye imagery and subsequent right eye imagery; display said subsequent left eye imagery on said left eye display; and display said subsequent right eye imagery on said right eye display; wherein said stereoscopic imaging system comprises a left camera and a right camera; and wherein said stereoscopic camera system image is configured to: use said left camera and said right camera of said stereoscopic camera system to perform said initial stereoscopic imaging of an area wherein said left camera has a location on said stereoscopic camera system, wherein said right camera has a location on said stereoscopic camera system, wherein said left camera's location and said right camera's location are separated by a stereoscopic distance, wherein said left camera has first pointing direction, and wherein said right camera has first pointing direction; change said left camera's first pointing direction to a second pointing direction wherein said left camera's second pointing direction is different than said left camera's first pointing direction, and wherein said left camera's second pointing direction points towards a convergence point; change said right camera's first pointing direction to a second pointing direction wherein said right camera's second pointing direction is different than said right camera's first pointing direction, and wherein said right camera's second pointing direction points towards said convergence point; and use said left camera and said right camera of said stereoscopic camera system to perform said subsequent stereoscopic imaging of said area with said left camera's second pointing direction and said right camera's second pointing direction.

Some embodiments comprise a stereoscopic smart phone comprising: a smart phone; and a stereoscopic imaging system operably connected to said smart phone comprising a left camera and a right camera wherein said stereoscopic camera system image is configured to: perform initial stereoscopic imaging of an area wherein said left camera has a location on said stereoscopic camera system, wherein said right camera has a location on said stereoscopic camera system, wherein said left camera's location and said right camera's location are separated by a stereoscopic distance, wherein said left camera has first pointing direction, and wherein said right camera has first pointing direction; change said left camera's first pointing direction to a second pointing direction wherein said left camera's second pointing direction is different than said left camera's first pointing direction, and wherein said left camera's second pointing direction points towards a convergence point; change said right camera's first pointing direction to a second pointing direction wherein said right camera's second pointing direction is different than said right camera's first pointing direction, and wherein said right camera's second pointing direction points towards said convergence point; use said left camera and said right camera of said stereoscopic camera system to perform subsequent stereoscopic imaging of said area with said left camera's second pointing direction and said right camera's second pointing direction.

In some embodiments a very high-resolution camera pair(s) could be used in connection with the type pairs described above. In some embodiments, there could be a disparity between the camera resolution and that of the display system wherein the camera resolution was greater (i.e., provided 'better resolution') than that of the display system. These very high-resolution camera pair(s) could be used in connection with changes in camera field of view (FOV). In some embodiments, the field of view could change (e.g., decrease in size) with a corresponding change of image resolution (e.g., increase in resolution). As an example, this embodiment could be used with a feedback mechanism wherein a user could, for example, start with a large FOV and then, thru a interactive cursor, indicate an area of interest and desired FOV. Then, the center point of the FOV would change to that point and the image area corresponding to that FOV and the resolution corresponding that FOV would create the image to be displayed.

The stereoscopic camera system has a variety of components, which include: aperture(s); lens(es); shutter(s); detector(s); mirror(s); and, display(s).

Aperture diameter would be consistent with the different lenses described below. Changeable or fixed type lenses or user selection of type lens chosen by the user. The current set of lenses within the smart devices is one option. Multi-shaped lenses (Note: this is analogous to reading glasses with variable portions of the lens based on look angle (e.g., top portion for looking straight forward and bottom portion for reading. This would be different to allow convergence (i.e., left lens and right lens in bottom portion would be canted differently.) Differing pointing angles can be based on the particular portion of the lens. Differing zoom can be based on the particular portion of the lens. Fisheye type lenses with high resolution. The idea is that different portions of the digital collection array would be associated with corresponding look angles through the fisheye lens The portion of the array which is used could be user specified. Alternatively, in some embodiments, automatic selection of the portion of the array selected could be based on input data from an inclinometer. Some embodiments comprise using a variable/differing radius of curvature. Some embodiments comprise using a variable/differing horizontal fields of view (FOV). Shutters timelines, etc. would be in accordance with the type technology chosen for the particular type detector array technology.

The standard types of detector arrays would be used for stereo camera pairs (for example, but not limited too. Collection array could include for example, but not limited to: charge couple devices (CCD), complementary metal-oxide semiconductor (CMOS). For camera systems needing a nighttime capability of operation, options would include, but are not limited to: low light level TVs; infrared detector arrays such as (mercury cadmium telluride (MCT); Indium gallium arsenide (InGaAs); quantum well infrared photodetector (QWIP).

Composite collection geometries of the collection array would be based on the desired viewing mode of the user. This would include, but would not be limited to: user selection of straight ahead for general viewing of the scene and specific objects at ranges greater that 20-30 feet where stereoscopic viewing becomes possible); variable convergence angles based upon the proximity of the object being viewed; to the left or to the right to provide a panoramic view (or, alternatively for scanning (e.g., left, to straight ahead, then to the right). Some embodiments comprise wherein a portion of the collection array would be facing straight ahead. Some embodiments comprise wherein a portion of the collection array would be constructed with different convergence angles. Some embodiments comprise wherein a portion of the collection array would be constructed with different look angles (left/right; far left/far right).

Left eye and right eye imagery could be merged and displayed on the smart device display. This composite image could then be viewed as by polarized glasses. Alternatively, the smart phone could be placed into a HDU with lenses to be converted into a virtual reality unit.

In some embodiments, the encasing framework of each of the lens could be rotated along 2 degrees of freedom (i.e., left/right and up/down). Alternatively, the encasing framework of the detector array could be rotated along 2 degrees of freedom (i.e., left/right and up/down). In some embodiments, a mirror(s) (or reflective surface) could be inserted to the stereo camera system. In a system configuration the user could rotate the mirror such that the desired viewing angles focused on the area/objects selected by the user.

In some embodiments, mechanical turning of the collection arrays or lenses or the entire camera. This mechanical turning would correspond with the user's desired viewing area (i.e., straight ahead or converged and some nearby location. This turning could be done electronically or by a physical mechanical linkage.

With respect to transmission, the first option would be for the person who collected the left and right eye data/imagery to view the stereo imagery on his/her head stereo display unit (HDU). This could be accomplished, for example, by a wire connection between the stereo phone and the stereo HDU. The user could also choose to send the stereo imagery to other persons. The transmission could be for single stereo pair(s) or streaming stereo video. The data transmitted could be interleafed (i.e., alternating between left eye data/imagery and right eye data/imagery). Alternatively, the data/imagery could be transmitted via multi channel with separate channels for left and right eye data/imagery. Alternatively, the left and right eye imagery frames could be merged for transmission. Using this technique, the HDU could use polarization or anaglyph techniques to ensure proper stereo display to the user. A further option would be store the left and right eye data/imagery. This storage could be accomplished by, but not limited to the following: on the smart device; on a removable device such as a memory stick; or on a portion of the cloud set aside for the user's storage. and at some later time download the stereo imagery to a device (e.g., computer) and subsequently displayed on a HDU.

There are a variety of modes of operations. Example modes of operation would include, but are not limited to the following: stereo snapshot; scanning; staring, tracking, and record then playback.

In some embodiments a very high-resolution camera pair(s) could be used in connection with the type pairs described above. In some embodiments, there could be a disparity between the camera resolution and that of the display system wherein the camera resolution was greater (i.e., provided 'better resolution') than that of the display system. These very high-resolution camera pair(s) could be used in connection with changes in camera field of view (FOV). In some embodiments, the field of view could change (e.g., decrease in size) with a corresponding change of image resolution (e.g., increase in resolution). As an example, this embodiment could be used with a feedback mechanism wherein a user could, for example, start with a large FOV and then, thru a interactive cursor, indicate an area of interest and desired FOV. Then, the center point of the FOV would change to that point and the image area corresponding to that FOV and the resolution corresponding that FOV would create the image to be displayed.

With respect to user interface, the type of control of the stereo camera pairs would be smart device dependent. For a smart phone device, for example, the principle screen could display a stereo camera icon.

Next, the Stereoscopic Head Display Unit (SHDU) will be discussed. Types of displays included both immersive (this could include, but would not be limited to: a very dark visor that can be brought down on the far side of the display to block viewing of the external scene; an electronic shutter external to the display and coincident with the HDU eyepieces could be of varying opacity) which could be initiated by the person wearing the head display unit; note that this); or mixed reality with a relative intensity/brightness of the intensity of the stereoscopic display relative to the external scene. A computer and memory would be integral to the HDU. A power supply would be integral to the HDU. The communications componentry would include, but is not limited to the following: communications port(s) (e.g., USB, HDMI, composite wire to connect to power source, smart device), antenna and receiver; associated circuitry. The audio componentry would include, but is not limited to: speakers, microphone, or both. A LRF is integral to 'smart device' and used to determine range from the smart device to the location of the object selected by the user to calculate convergence angles for left and right viewing angles to provide proper stereoscopic images. In addition, a pseudo-GPS system can be integrated as described in U.S. Pat. No. 10,973,485, which is incorporated by reference in its entirety.

In some embodiments, stereoscopic image processing will be performed on the images produced by the two stereoscopic cameras. One of the image processing techniques is image enhancement. These enhancement techniques include but are not limited to the following: noise reduction, deblurring, sharpening and softening the images, filtering, etc. In an example of noise reduction, there would be two separate images each of which would undergo a separate noise reduction process. (Note that noise is random in nature and, therefore, a different set of random noise would occur in the left camera image from right camera. And, after the consequent reduction, a different set of pixels would remain in the two images.) Given these images were taken beyond the stereoscopic range, then the two images could be merged resulting a more comprehensive, noise free image. In some embodiments, stereoscopic image processing will include segmentation. These enhancement techniques include but are not limited to the following: edge detection methods; histogram-based methods; tree/graph based methods; neural network based segmentation; thresholding; clustering methods; graph partitioning methods; watershed transformation; probabilistic; and Bayesian approaches. Given these images were taken beyond the stereoscopic range, a different technique for left and right images could be invoked. If the segmentation produced identical results, then there would be higher confidence in results. If the results were different, however, then a third segmentation method could be invoked and an adjudication process resolve the segmentation.

In some embodiments of stereoscopic image processing, a set of left and right images would be produced over time. The user could identify an object(s) of interest which could be tracked over time. Stereoscopic image processing consisting of background suppression could be applied to both left and right images which could enhance stereoscopic viewing of the object(s) of interest. In some embodiments of stereoscopic image processing, false color could be added to the scene and/or object(s) of interest within the scene. An example of stereoscopic image processing, would be to use opposing anaglyph colors for left and right eye images. A further example would be to use color figures to provide augmented reality of stereoscopic images.

In some embodiments of stereoscopic image processing, would be image compression for data storage and transmission. As an example for compression as it applies to of stereoscopic image processing would be to: for portions of an image beyond stereoscopic ranges, apply stereoscopic image compression processing (to include but not limited to am-length encoding) to only that region to one of either left or right images, but not both. For that region that is within stereoscopic ranges, apply stereoscopic image compression processing to both the left and right images.

In some embodiments of stereoscopic image processing would include morphological processing which would include but not limited to: dilation, erosion, boundary extraction, region filling. An example for morphological processing as it applies to of stereoscopic image processing would be to perform erosion for the left image but not for the right. Left and right images could be alternated to permit the user to evaluate whether this type of processing was desirable.

In some embodiments of stereoscopic image processing, stereoscopic object recognition would be invoked. Techniques for stereoscopic object recognition include but are not limited to: convolutional neural networks (CNNs); and support vector machines (SVM). A number of support features include, but are not limited to: feature extraction; pattern recognition, edge detection; and corner detection. Examples of automated object recognition (AOR) processing as it applies to of stereoscopic image processing would be to: recognize brands of cars; recognize types of animals, optical character reading; optical character reading coupled with a translation dictionary. For example, CNN AOR could be performed on left camera imagery and SVM on right camera imagery. If both agree on the type Object, that type object is presented to the user. However, if agreement is not reached by CNN and SVM, then a third type of recognition methodology such as feature recognition would be invoked.

In some embodiments of stereoscopic image processing would include image stabilization would be invoked. If a single stereoscopic image was desired by the user and if upon review of the image, the image was blurred due to vibration or movements) of the stereoscopic cameras during the imaging interval then an option would be to decrease the shutter interval and repeat the stereoscopic image collection. If, however, a stereoscopic video collection was to be obtained by the user, then stereoscopic image processing would include, but not be limited to: selection of three or more reference points within the stereoscopic images (i.e., visible in both left and right images) and, from frame to sequential frame, adjust the sequential frame(s) to align the reference points; a border surrounding the displayed stereoscopic images could be invoked to reduce the overall area of the stereoscopic images.

In some embodiments, stereoscopic viewing of the virtual 3D mannequin is performed on an extended reality display unit, which is described in U.S. Pat. No. 8,384,771, METHOD AND APPARATUS FOR THREE DIMENSIONAL VIEWING OF IMAGES, which is incorporated by reference in its entirety. This patent teaches image processing techniques including volume generation, filtering, rotation, and zooming.

In some embodiments, stereoscopic viewing of the virtual 3D mannequin is performed with convergence, which is described in U.S. Pat. No. 9,349,183, METHOD AND APPARATUS FOR THREE DIMENSIONAL VIEWING OF IMAGES, which is incorporated by reference in its entirety. This patent teaches shifting of convergence. This feature can be used in combination with filtering.

In some embodiments, stereoscopic viewing can be performed using a display unit, which incorporates polarized lenses, which is described in U.S. Pat. No. 9,473,766, METHOD AND APPARATUS FOR THREE DIMENSIONAL VIEWING OF IMAGES, which is incorporated by reference in its entirety.

In some embodiments, advancements to display units can be incorporated for viewing the virtual 3D mannequin, which are taught in U.S. patent application Ser. No. 16/828, 352, SMART GLASSES SYSTEM and U.S. patent application Ser. No. 16/997,830, ADVANCED HEAD DISPLAY UNIT FOR FIRE FIGHTERS, which are both incorporated by reference in their entirety.

In some embodiments, advancements in display units are taught in U.S. patent application Ser. No. 17/120,109, ENHANCED VOLUME VIEWING, which is incorporated by reference in its entirety. Included herein is a head display unit, which is improved by incorporating geo-registration.

Some embodiments comprise utilizing an improved field of view on an extended reality head display unit, which is taught in U.S. patent application Ser. No. 16/893,291, A METHOD AND APPARATUS FOR A HEAD DISPLAY UNIT WITH A MOVABLE HIGH RESOLUTION FIELD OF VIEW, which is incorporated by reference in its entirety.

In some embodiments, image processing steps can be performed using a 3D volume cursor, which is taught in U.S. Pat. No. 9,980,691, METHOD AND APPARATUS FOR THREE DIMENSIONAL VIEWING OF IMAGES, and U.S. Pat. No. 10,795,457, INTERACTIVE 3D CURSOR, both of which are incorporated by reference in its entirety.

In some embodiments, a precision sub-volume can be utilized in conjunction with the virtual 3D mannequin, which is taught in U.S. patent application Ser. No. 16/927, 886, A METHOD AND APPARATUS FOR GENERATING A PRECISION SUB-VOLUME WITHIN THREE-DIMENSIONAL IMAGE DATASETS, which is incorporated by reference in its entirety.

In some embodiments, viewing of a structure at two different time points can be performed using a ghost imaging technique, which is taught in U.S. Pat. No. 10,864,043, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, which is incorporated by reference in its entirety.

Some embodiments comprise selecting a specific surgical device for pre-operative planning, which is taught in U.S. patent application Ser. No. 17/093,322, A METHOD OF SELECTING A SPECIFIC SURGICAL DEVICE FOR PREOPERATIVE PLANNING, which is incorporated by reference in its entirety.

Some embodiments comprise, generating the virtual 3D mannequin using techniques described in U.S. patent application Ser. No. 16/867,102, METHOD AND APPARATUS OF CREATING A COMPUTER-GENERATED PATIENT SPECIFIC IMAGE, which is incorporated by reference in its entirety. Key techniques include using patient factors (e.g., history, physical examination findings, etc.) to generate a volume.

Some embodiments comprise advanced image processing techniques available to the user of the virtual 3D mannequin, which are taught in U.S. Pat. No. 10,586,400, PROCESSING 3D MEDICAL IMAGES TO ENHANCE VISUALIZATION, and U.S. Pat. No. 10,657,731, PROCESSING 3D MEDICAL IMAGES TO ENHANCE VISUALIZATION, both of which are incorporated by reference in its entirety.

Some embodiments comprise performing voxel manipulation techniques so that portions of the virtual 3D mannequin can be deformed and move in relation to other portions of the virtual 3D mannequin, which is taught in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

Some embodiments comprise generating at least some portions of the virtual 3D mannequin through artificial intelligence methods and performing voxel manipulation thereof, which is taught in U.S. patent application Ser. No. 16/736,731, RADIOLOGIST-ASSISTED MACHINE LEARNING WITH INTERACTIVE, VOLUME SUBTENDING 3D CURSOR, which is incorporated by reference in its entirety.

Some embodiments comprise wherein at least some component of the inserted 3D dataset into the virtual 3D mannequin are derived from cross-sectional imaging data fine tuned with phantoms, which is taught in U.S. patent application Ser. No. 16/752,691, IMPROVING IMAGE QUALITY BY INCORPORATING DATA UNIT ASSURANCE MARKERS, which is incorporated by reference in its entirety.

Some embodiments comprise utilizing halo-type segmentation techniques, which are taught in U.S. patent application Ser. No. 16/785,606, IMPROVING IMAGE PROCESSING VIA A MODIFIED SEGMENTED STRUCTURE, which is incorporated by reference in its entirety.

Some embodiments comprise using techniques for advanced analysis of the virtual 3D mannequin taught in U.S. patent application Ser. No. 16/939,192, RADIOLOGIST ASSISTED MACHINE LEARNING, which are incorporated by reference in its entirety.

Some embodiments comprise performing smart localization from a first virtual 3D mannequin to a second virtual 3D mannequin, such as in an anatomy lab, which is performed via techniques taught in U.S. patent application Ser. No. 17/100,902, METHOD AND APPARATUS FOR AN IMPROVED LOCALIZER FOR 3D IMAGING, which is incorporated by reference in its entirety.

Some embodiments comprise performing a first imaging examination with a first level of mechanical compression and a second imaging examination with a second level of mechanical compression and analyzing differences therein, which is taught in U.S. patent application Ser. No. 16/594,139, METHOD AND APPARATUS FOR PERFORMING 3D IMAGING EXAMINATIONS OF A STRUCTURE UNDER DIFFERING CONFIGURATIONS AND ANALYZING MORPHOLOGIC CHANGES, which is incorporated by reference in its entirety.

Some embodiments comprise displaying the virtual 3D mannequin in an optimized image refresh rate, which is taught in U.S. patent application Ser. No. 16/842,631, A SMART SCROLLING SYSTEM, which is incorporated by reference in its entirety.

Some embodiments comprise displaying the virtual 3D mannequin using priority volume rendering, which is taught in U.S. Pat. No. 10,776,989, A METHOD AND APPARATUS FOR PRIORITIZED VOLUME RENDERING, which is incorporated by reference in its entirety.

Some embodiments comprise displaying the virtual 3D mannequin using tandem volume rendering, which is taught in U.S. patent Ser. No. 17/033,892, A METHOD AND APPARATUS FOR TANDEM VOLUME RENDERING, which is incorporated by reference in its entirety.

Some embodiments comprise displaying images in a optimized fashion by incorporating eye tracking, which is taught in U.S. patent application Ser. No. 16/936,293, IMPROVING VISUALIZATION OF IMAGES VIA AN ENHANCED EYE TRACKING SYSTEM, which is incorporated by reference in its entirety.

Some embodiments comprise enhancing collaboration for analysis of the virtual 3D mannequin by incorporating teachings from U.S. patent application Ser. No. 17/072,350, OPTIMIZED IMAGING CONSULTING PROCESS FOR RARE IMAGING FINDINGS, which is incorporated by reference in its entirety.

Some embodiments comprise improving multi-user viewing of the virtual 3D mannequin by incorporating teachings from U.S. patent application Ser. No. 17/079,479, AN IMPROVED MULTI-USER EXTENDED REALITY VIEWING TECHNIQUE, which is incorporated by reference in its entirety.

Some embodiments comprise improving analysis of images through use of geo-registered tools, which is taught in U.S. Pat. No. 10,712,837, USING GEO-REGISTERED TOOLS TO MANIPULATE THREE-DIMENSIONAL MEDICAL IMAGES, which is incorporated by reference in its entirety.

Some embodiments comprise integration of virtual tools with geo-registered tools, which is taught in U.S. patent application Ser. No. 16/893,291, A METHOD AND APPARATUS FOR THE INTERACTION OF VIRTUAL TOOLS AND GEO-REGISTERED TOOLS, which is incorporated by reference in its entirety.

In some embodiments blood flow is illustrated in the virtual 3D mannequin, which is taught in U.S. patent application Ser. No. 16/506,073, A METHOD FOR ILLUSTRATING DIRECTION OF BLOOD FLOW VIA POINTERS, which is incorporated by reference in its entirety and U.S. Pat. No. 10,846,911, 3D IMAGING OF VIRTUAL FLUIDS AND VIRTUAL SOUNDS, which is also incorporated by reference in its entirety.

Some embodiments also involve incorporation of 3D printed objects to be used in conjunction with the virtual 3D mannequin. Techniques herein are disclosed in U.S. patent Ser. No. 17/075,799, OPTIMIZING ANALYSIS OF A 3D PRINTED OBJECT THROUGH INTEGRATION OF GEO-REGISTERED VIRTUAL OBJECTS, which is incorporated by reference in its entirety.

Some embodiments also involve a 3D virtual hand, which can be geo-registered to the virtual 3D mannequin. Techniques herein are disclosed in U.S. patent application Ser. No. 17/113,062, A METHOD AND APPARATUS FOR A GEO-REGISTERED 3D VIRTUAL HAND, which is incorporated by reference in its entirety.

Some embodiments comprise utilizing images obtained from U.S. patent application Ser. No. 16/654,047, METHOD TO MODIFY IMAGING PROTOCOLS IN REAL TIME THROUGH IMPLEMENTATION OF ARTIFICIAL, which is incorporated by reference in its entirety.

Some embodiments comprise utilizing images obtained from U.S. patent application Ser. No. 16/597,910, METHOD OF CREATING AN ARTIFICIAL INTELLIGENCE GENERATED DIFFERENTIAL DIAGNOSIS AND MANAGEMENT RECOMMENDATION TOOL BOXES DURING MEDICAL PERSONNEL ANALYSIS AND REPORTING, which is incorporated by reference in its entirety.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A illustrates the back of a smart phone with stereoscopic camera capability.

FIG. 1B illustrates the front of a smart phone with stereoscopic camera capability.

FIG. 2A illustrates key components of the smart phone with stereoscopic camera capability.

FIG. 2B illustrates a top down view of the smart phone with stereoscopic camera capability.

FIG. 2C illustrates a top down view of the smart phone with stereoscopic camera capability with convergence.

FIG. 3A illustrates curved lens concept for smart phone with stereoscopic camera capability.

FIG. 3B illustrates fish-eye type of lens concept for smart phone with stereoscopic camera capability.

FIG. 3C illustrates a progressive type of lens concept for smart phone with stereoscopic camera capability.

FIG. 4A illustrates a front view of a composite sensor array concept for a smart phone with stereoscopic camera capability.

FIG. 4B illustrates a top view of a composite sensor array concept for a smart phone with stereoscopic camera capability.

FIG. 5A illustrates a front view of a flat mirror concept for smart phone with stereoscopic camera capability.

FIG. 5B illustrates a top-down view of the flat mirror concept for smart phone with stereoscopic camera capability.

FIG. 5C illustrates a front view of a curved mirror concept for smart phone with stereoscopic camera capability.

FIG. 5D illustrates a top-down view of the curved mirror concept for smart phone with stereoscopic camera capability.

FIG. 5E illustrates a front view of a deformable mirror concept for smart phone with stereoscopic camera capability.

FIG. 5F illustrates a top-down view of the deformable mirror concept for smart phone with stereoscopic camera capability at time equals 1.

FIG. 5G illustrates a top-down view of the deformable mirror concept for smart phone with stereoscopic camera capability at time equals 2.

FIG. 6A illustrates a movable lens for smart phone with stereoscopic camera capability.

FIG. 6B illustrates the composite sensor array concept.

FIG. 6C illustrates a switching out of cameras from Day 1 to Day 2.

FIG. 7A illustrates the Stereoscopic Head Display Unit (SHDU).

FIG. 7B shows a side view of a transformable SHDU display unit with an eyepiece cover with augmented reality mode and virtual reality mode.

FIG. 7C shows a side view of a transformable SHDU display unit with an electronic eye piece with augmented reality mode and virtual reality mode.

FIG. 8A illustrates wired connectivity means between smart phone with stereoscopic camera capability and stereoscopic head display unit.

FIG. 8B illustrates wireless connectivity via BlueTooth means between smart phone with stereoscopic camera capability and stereoscopic head display unit.

FIG. 8C illustrates wireless connectivity via the Internet means between smart phone with stereoscopic camera capability and stereoscopic head display unit.

FIG. 9A illustrates system operation using the stereoscopic smart phone (SSP).

FIG. 9B illustrates near real-time stereo mode at time N.

FIG. 9C illustrates near real-time stereo mode at time N+1.

FIG. 9D illustrates convergence mode at time N+1.

FIG. 10A illustrates before application of automatic object recognition as displayed on the stereoscopic head display unit.

FIG. 10B illustrates after application of automatic object recognition as displayed on the stereoscopic head display unit.

FIG. 10C invokes another stereo camera unique technology.

FIG. 11A illustrates integration of image stabilization for a user in a scene where there is vibration.

FIG. 11B illustrates selection of points within the image to use for image stabilization.

FIG. 11C illustrates illustrates selection of points within the scene to use for image stabilization.

FIG. 11D illustrates stereoscopic image stabilization on the SHDU.

FIG. 12A illustrates determining a stabilization point and field of view (FOV) for the left eye imagery and right eye imagery.

FIG. 12B illustrates displaying stabilized stereoscopic imagery on a SHDU.

FIG. 13A illustrates a stereoscopic smart phone (SSP) with its stereoscopic cameras in a first position, which is wide.

FIG. 13B illustrates the SSP with its stereoscopic cameras in a second position, which is narrow.

FIG. 13C illustrates the SSP with its stereoscopic cameras in a third position, which is also narrow, but shifted in position as compared to FIG. 12B.

DETAILED DESCRIPTION

Figure 14:
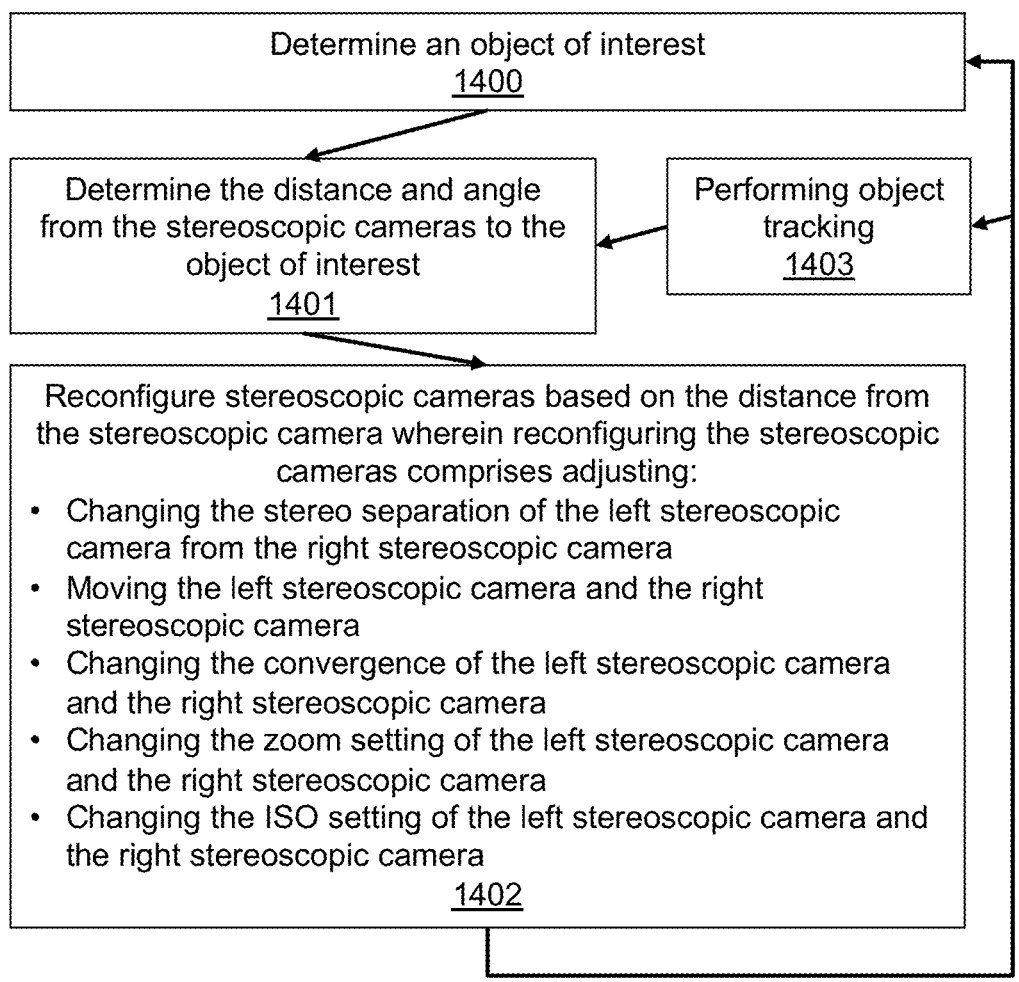
FIG. 14 illustrates optimizing stereoscopic imaging.

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

FIG. 1A illustrates the back of a smart phone with stereoscopic camera capability. This is called a stereoscopic smart phone (SSP). 101 illustrate a smart phone with stereoscopic camera capability. 102 illustrates a first outward facing camera on the back of the smart phone 101. 103 illustrates a second outward facing camera on the back of the smart phone 101. The first camera 102 and the second camera 103 are separated by a stereoscopic distance. In the preferred embodiment, these would be maximally separated to enhance stereo separation to achieve stereoscopic vision at distances greater than a user could with his/her own stereoscopic distance. Some embodiments comprise placing mechanical extensions to further increase the stereo separation. In some embodiments, two phones would work in conjunction to further increase stereo distance. For example, a first smart phone could be placed in 10, 20 or 30 feet from a second smart phone. The video imagery could be synchronized and video imagery from a camera from the first phone and video imagery from a camera from the second phone can be used together to generate stereoscopic imagery. In some embodiments, these phones are to be manufactured with differing stereoscopic distances. In some embodiments, the stereoscopic distance can match that of a person. Some designs will therefore have a larger stereoscopic distance and other designs will have a smaller stereoscopic distance.

FIG. 1B illustrates the front of a smart phone with stereoscopic camera capability. 104 illustrates a third outward facing camera on the front of the smart phone 101. 105 illustrates a fourth outward facing camera on the front of the smart phone 101. The third camera 104 and the fourth camera 105 are separated by a stereoscopic distance. 106 illustrates the display portion of the smart phone. As with today's smart phones, different sizes of phones are available with the consequent increases in the surface area of the larger phones. 107 represent a location on the smart phone for wired communication, such as for power (recharge battery) and/or external input/output of digital data. In the case of the smart phone with stereoscopic cameras capability, 108 would provide the port where a wire connection could communicate with the stereoscopic head display unit. 108 is example location of ON/OFF switch. 109 illustrates a volume up control button. 110 illustrates a volume down control button. 111 is the input/output antenna. This antenna would support communications with the Stereoscopic Head Display Unit.

FIG. 2A illustrates key components of the smart phone with stereoscopic camera capability. 200 illustrates a listing of the key components of the smart phone with stereoscopic cameras capability. These components are the same for both cameras. First, there is the aperture which look outward through the two holes in the back of the phone and front of the phone as described in FIG. 1. Next, there is a shutter with a variable speed. The is followed by a lens which will be described in some detail in subsequent figures. Depending on the detailed layout of the components, it is novel to insert a mirror to redirect the light which has passed through the lens to the sensor array which will be illustrated in subsequent figures. In some embodiments, the mirror is a deformable mirror. In some embodiments, the mirror is capable of working with adaptive optics. In some embodiments, the mirror is a curved mirror. In some embodiments, the mirror is a flat mirror. A processor and software support the operation of the camera system. For example, changing the camera viewing angle from looking straight forward to convergence mode where the left camera would look down and the right and the right camera would down and to the left. These viewing angles would intersect at a convergence point on the object of interest. These angles would be based on the proximity of the object of interest to the cameras. Depending on the design option selected there may be mechanical elements that interact with either components or the camera as a whole. There is the display which is part of the phone. Finally, there is communications link which transport data in for the mode of operation and data out to the display. Note that concepts taught in this patent are preferred to be placed in a smart phone; however, could be used in other smart devices.

FIG. 2B illustrates a top-down view of the smart phone with stereoscopic camera capability. 200 illustrates a smart phone. 201F illustrates the front face of a smart phone. 201B illustrates the back of the smart phone. 202 illustrates a first camera of a stereoscopic camera pair, which is pointed in orthogonal to the front of the smart phone 201F. 202A illustrates the center angle of the first camera 202, which is the direction to the center of the field of view of the first camera 202. 203 illustrates a second camera of a stereoscopic camera pair, which is pointed in orthogonal to the front of the smart phone 201F. 203A illustrates the center angle of the second camera 203, which is the direction to the center of the field of view of the second camera 203.

FIG. 2C illustrates a top-down view of the smart phone with stereoscopic camera capability with convergence. In the preferred embodiment, this is performed using the same smart phone and the cameras alter the direction from which imagery is obtained. In the preferred embodiment, this is performed based on altering configuration of the componentry of the camera. In other embodiments, this is performed digitally, as is taught in U.S. Ser. No. 17/225,610, AN IMPROVED IMMERSIVE VIEWING EXPERIENCE filed on Apr. 8, 2021 and U.S. patent application Ser. No. 17/237,152, AN IMPROVED IMMERSIVE VIEWING EXPERIENCE, filed on Apr. 22, 2021, which are incorporated by reference in their entirety. 200 illustrates a smart phone. 201F illustrates the front face of a smart phone. 201B illustrates the back of the smart phone. 202 illustrates a first camera of a stereoscopic camera pair. 202B illustrates the center angle of the first camera 202, which is the direction to the center of the field of view of the first camera 202. 203 illustrates a second camera of a stereoscopic camera pair. 203B illustrates the center angle of the second camera 203, which is the direction to the center of the field of view of the second camera 203. Note that the center angle 202B of the first camera of the first camera 202 and the center angle 203B of the second camera 203 are both canted inward towards each other towards a convergence point "204". In the preferred embodiment, the convergence point is in the midline (along the plane orthogonal to the front of the smart phone 201 from a point half way in between the first camera 202 and the second camera 203). In some embodiments, the convergence point can be: at the level of the first camera 202 and the second camera 203; above the level of the first camera 202 and the second camera 203; below the level of the first camera 202 and the second camera 203; or, off of midline. The convergence point can be any point in (x, y, z) space seen by the first camera 202 and second camera 203. In some embodiments, if the relative positions of two smart devices are known, a camera from the first smart device and a camera from the second smart device can also be used to yield stereoscopic imagery, as taught in this patent and in the patents incorporated by reference in their entirety.

FIG. 3A illustrates curved lens concept for smart phone with stereoscopic camera capability. This figure illustrates the first of three concepts for lenses for the smart phone with stereoscopic cameras capability. 301 illustrates a curved lens with an angular field of regard 302 and with a radius of curvature of 303. The camera would also have a variable field of view which would be pointed somewhere within the field of regard.

FIG. 3B illustrates fish-eye type of lens concept for smart phone with stereoscopic camera capability. 304 illustrates a fish-eye type of lens. This lens could provide hemi-spherical or near hemispherical coverage 305.

FIG. 3C illustrates a progressive type of lens concept for smart phone with stereoscopic camera capability. 306 illustrates a first progressive type of lens, which can be used for the first camera of a stereoscopic camera pair. 307 illustrates a portion of the lens that optimizes image acquisition in a straight-forward direction. 308 illustrates a portion of the lens that provides an increasingly focused capability wherein there is a greater magnification as compared to 307. 308 is directly associated with convergence at shorter and shorter distances. Note that 308 is located towards the bottom and towards the second camera of a stereoscopic camera pair. 310 illustrates a second progressive type of lens, which can be used for the second camera of a stereoscopic camera pair. 311 illustrates a portion of the lens that optimizes image acquisition in a straight-forward direction. 312 illustrates a portion of the lens that provides an increasingly focused capability wherein there is a greater magnification as compared to 311. 312 is directly associated with convergence at shorter and shorter distances. Note that 312 is located towards the bottom and towards the first camera of a stereoscopic camera pair. Together, these provide a unique capability to the smart phone with stereoscopic cameras. A progressive lens has a corrective factor to provide looking straight forward and in a 'progressive' manner gradually increases magnification in a downward and inward direction through the progressive lens. Note that electronic correction can occur to account for refraction through the lens. In some embodiments, the amount of magnification can be increased in the medial or inferior-medial direction. This can be performed for eyeglasses, which is referred to as "convergence type progressive eyeglasses".

FIG. 4A illustrates a front view of a composite sensor array concept for a smart phone with stereoscopic camera capability.

This figure illustrates a novel arrangement of individual sensor arrays 401. This array would be for the left camera—a mirror image of this arrangement would be used in the right camera. Note that there could be an upper layer(s) and a lower layer(s) of composite sensor arrays. Going from left to right, there are five different arrays, array #1 402, array #2 403, array #3 404, array #4 405, array #5 406, and collectively, this creates the of composite sensor arrays.

FIG. 4B illustrates a top view of a composite sensor array concept for a smart phone with stereoscopic camera capability. Nominally, 402 points 60 degrees left of center; 402 points 30 degrees left of center; 404 points straight forward; 405 points 30 degrees to the right of center; and 406 points 60 degrees to the right of center. If there were a second and lower row. These arrays could be canted downward. Similarly, if there were an additional row in an upper position, these arrays could be canted upward.

FIG. 5A illustrates a flat mirror concept for smart phone with stereoscopic camera capability. This is the first of three mirror (or reflective surface) concepts which could be inserted into the stereoscopic cameras. A mirror, if included in the design, would in the preferred embodiment be placed between the lens and the detection sensors mirror to redirect the light which has passed through the lens to the sensor array. This front view illustrates a typical flat mirror 501. 502 is the mirror frame.

FIG. 5B illustrates a top-down view of a flat mirror concept for smart phone with stereoscopic camera capability. 502 shows the outline of the frame. 501 shows the mirror which is hidden by the frame.

FIG. 5C illustrates a front view of a curved mirror concept for smart phone with stereoscopic camera capability. 503 illustrates a curved mirror encased by a frame 504.

FIG. 5D illustrates a front view of a curved mirror concept for smart phone with stereoscopic camera capability. 503 illustrates the curved mirror encased by a frame 504. In the preferred embodiment, a spherical-type curvature is used. In some embodiments, a cylindrical-type curvature is used. In some embodiments, the curvature can include both spherical-type curvature and cylindrical-type curvatures. In some embodiments, multiple (at least two) different curved mirrors can be used. For example, if for a long range zooming, a first type of curved mirror can be utilized. If for medium range zooming, a second type of curved mirror can be utilized. These can be used one at a time, so the first type of curved mirror and second type of curved mirror can be swapped out depending on what object is being viewed.

FIG. 5E illustrates a front view of a deformable mirror concept for smart phone with stereoscopic camera capability. 505 illustrates a deformable mirror encased by a frame 506. An inventive aspect of this patent is to use a deformable mirror in conjunction with a stereoscopic camera system.

FIG. 5F illustrates a top-down view of the deformable mirror concept for smart phone with stereoscopic camera capability at time equals 1. 505 illustrates a deformable mirror encased by a frame 506. Note the contour of the deformable mirror at this first time point.

FIG. 5G illustrates a top-down view of the deformable mirror concept for smart phone with stereoscopic camera capability at time equals 2. 505 illustrates a deformable mirror encased by a frame 506. Note the contour of the deformable mirror at this second time point, which is different from the contour at the first time point. At a first time point, for the first camera the curvature of the first deformable mirror has a first focal point. At a second time point, for the first camera the curvature of the first deformable mirror has a second focal point, which is different from the first focal point. At a first time point, for the second camera the curvature of the second deformable mirror has a first focal point. At a second time point, for the second camera the curvature of the second deformable mirror has a second focal point, which is different from the first focal point. Thus, at the first time point the first deformable mirror and second deformable mirror would optimize imagery at a first location. This could be an object in the scene or a point in space. This could be a first convergence point. Thus, at the second time point the first deformable mirror and second deformable mirror would optimize imagery at a second location. This could be an object in the scene or a second location. This could be a second convergence point. The second convergence point would be different from the first convergence point. The deformable system is inventive because it maintains high light collection and can rapidly alter the projection of this light from the scene onto the detector. In some embodiments, eye tracking of a user is performed. Based on eye tracking metrics of a user, the deformable mirrors deform to optimize image acquisition from those areas. This includes a location where a user is looking. Thus, imagery collected can be optimized based on where a user is looking. Thus, as the user looks a new objects via saccades movements of his/her eyes, the stereoscopic deformable mirror system can deform to adapt to new areas where the user is looking. Similarly, as the user tracks objects as it moves with smooth tracking movements of his/her eyes, user is looking. Thus, imagery collected can be optimized based on where a user is looking. Thus, as the user looks a new objects via saccades movements of his/her eyes, the stereoscopic deformable mirror system can deform to adapt to new areas where the user is looking.

FIG. 6A illustrates a movable lens for smart phone with stereoscopic camera capability. This figure is the first of three different potential of the smart phone with stereoscopic cameras capability. FIG. 6A depicts a movable lens which could be used to change the look angle. Light 601 is shown as a series of parallel wavy lines entering the lens 602. In this case, the lens is the progressive type lens described in FIG. 3C. The position of the lens at Time 1 is such that the light enters the top portion of the lens which imagery looking straight forward and no convergence point for the left and right viewing angles is used. At Time 2, the position of the lens has shifted upward and the light 601 now enters the bottom portion of the lens 604. The bottom right portion of the left lens causes the look angle to shift down and to the right. The bottom left portion of the right lens causes the look angle to shift down and to the left. Under this configuration, the viewing angles of the left and right lenses intersect (i.e., converge) and, collectively, provide a stereoscopic view.

FIG. 6B illustrates the composite sensor array concept. The light has already passed through the lens and is converging on one of the sensor arrays of the composite sensor arrays described for FIG. 4. At Time 1. the light enters the center array 608 and provides looking straight ahead imagery. At Time 2, the array has rotated, and the light impinges, in this case, on sensor array 609. Thus, the viewing angles from the left and right cameras intersect and provide stereoscopic imagery.

FIG. 6C illustrates a switching out of cameras from Day 1 to Day 2. Note this could be analogous switching lenses on today's digital cameras. On Day 1, 611 shows the camera box; 612 the aperture, 613 the shutter; 614 the lens; 615 the sensor array and 616 the communications port. On day 2, the user selects a different; takes out the camera used on day 1 and inserts a totally different camera 617 of the same size and shape as the camera uses on Day 1. On Day 2, the aperture 618 is larger and the lens 621 has a curvature. 620 illustrates the shutter. 622 the sensor array and 623 the communications port. In some embodiments, the cameras can be stored on the smart phone and swapped out through mechanical processes on the smart phone. In other embodiments, swapping out can be through manual processes, as is done with today's SLR cameras. Collectively, FIG. 6A, FIG. 6B and FIG. 6C demonstrate the flexibility of the smart phone with stereoscopic cameras.

FIG. 7A illustrates the Stereoscopic Head Display Unit (SHDU). This figure illustrates key aspects of the Stereoscopic Head Display Unit. FIG. 7A shows example placements of key components of the SHDU. 701 illustrates the overall headset. 702 illustrates the left eye display. 702A illustrates the left eye tracking device. 703 illustrates the right eye display. 703A illustrates the right eye tracking device. 704 illustrates the processor. 705 illustrates the left ear speaker. 706 illustrates the power supply. 707 illustrates the antenna. 708 illustrates the right ear speaker. 709 illustrates the inclinometer (or inertial measurement unit). 710 illustrates the microphone. 711 illustrates the communications port. 712 illustrates a scene sensing device.

FIG. 7B shows a side view of a transformable SHDU display unit with an eyepiece cover with augmented reality mode and virtual reality mode. 713A illustrates the side of the frame of the SHDU 701 at Time Point #1. 714A illustrates an eye piece cover. In the preferred embodiment, the eyepiece cover is connected to the SHDU 701 via a hinge. This is called a transformable SHDU because it can transform from a virtual reality type display (where the real world is blocked out) to an augmented reality type display (where the user can see both the virtual world and the real world). Thus, at Time Point #1, the transformable SHDU is in augmented reality mode. The eye piece cover is in the elevated position and does not block the wearer of the SHDU from seeing the external area around him/her. If the wearer is concurrently viewing virtual imagery (e.g., stereoscopic imagery from smart phone with stereoscopic cameras), this would constitute augmented mixed reality. 713B illustrates the side of the frame of the SHDU 701 at Time Point #2. 714B illustrates an eye piece cover, which is now in position over the front of the SHDU, so it is in virtual reality mode at Time Point #2. At Time Point #2, the eye piece cover has rotated down and now covers the eye piece. The wearer of the SHDU would be blocked from seeing the external area around him/her. If the wearer is concurrently viewing stereoscopic imagery from smart phone with stereoscopic cameras, this would constitute virtual reality.

FIG. 7C shows a side view of a transformable SHDU display unit with an electronic eye piece with augmented reality mode and virtual reality mode. 713C illustrates the side of the frame of the SHDU 701 at Time Point #1. 714C illustrates an electronic eye piece affixed the SHDU 701 at Time Point #1. At Time Point #1, the setting for the electronic eye piece is transparent and light 715C is able to pass through unfiltered on the SHDU display units. Thus, this is augmented reality mode because the user can see both the real world and the virtual world. 713D illustrates the side of the frame of the SHDU 701 at Time Point #2. 714D illustrates an electronic eye piece affixed the SHDU 701 at Time Point #2. At Time Point #2, the setting for the electronic eye piece is opaque and light 715D is not able to pass through unfiltered on the SHDU display units. Thus, this is virtual reality mode because the user can only see the virtual world. In some embodiments, the opacity ranges in varying degrees of opacity. Thus, the electronic eye piece can a range of realities—mixed reality to virtual reality.

FIG. 8A illustrates wired connectivity means between smart phone with stereoscopic camera capability and stereoscopic head display unit. FIG. 8A is the first of three principle connectivity means between the stereoscopic smart phone (SSP) and stereoscopic head display unit (SHDU). FIG. 8A shows the front side of the SSP 800A connected to the SHDU 801A via a wire 802. The stereoscopic imagery would be available on both the smart phone display 800A and the SHDU 801A. There are multiple options of what to display on the smart phone display: single left eye image or right eye image filling the entire display; both left eye image and right eye image on a split screen display; a merged left and right eye image to be viewed by a user wearing polarized or anaglyph glasses. In some embodiments, the SSP could be worn on a first user's head and imagery obtained from the stereoscopic cameras on the back of the SSP as in FIG. 1A. In addition, the imagery obtained from the back stereoscopic cameras on the back of the SSP could be displayed on the SHDU worn by a second user. This would allow the second user to view the same imagery as the first user, which can be displayed in near real time. In some embodiments, stereoscopic imagery obtained from the SHDU could be sent to the SSP.

FIG. 8B illustrates wireless connectivity via BlueTooth means between smart phone with stereoscopic camera capability and stereoscopic head display unit. In this embodiment, the stereoscopic imagery would be transmitted from the SSP 800B via a BlueTooth connection 803 to the SHDU 801B which would be received through the SHDU's antenna and subsequently routed to the processor and thence to the SHDU's left and right displays. In addition, the imagery obtained from the back stereoscopic cameras on the back of the SSP could be displayed on the SHDU 801B worn by a second user. This would allow the second user to view the same imagery as the first user, which can be displayed in near real time. In some embodiments, stereoscopic imagery obtained from the SHDU could be sent to the SSP for display, as discussed in FIG. 8A.

FIG. 8C illustrates wireless connectivity via the Internet means between smart phone with stereoscopic camera capability and stereoscopic head display unit. In this embodiment, the stereoscopic imagery would be transmitted from the SSP 800C via an Internet connection 804 to the SHDU 801C which would received through the SHDU antenna and subsequently routed to the processor and thence to the SHDU left and right displays. In addition, the imagery obtained from the back stereoscopic cameras on the back of the SSP could be displayed on the SHDU 801C worn by a second user. This would allow the second user to view the same imagery as the first user, which can be displayed in near real time. In some embodiments, stereoscopic imagery obtained from the SHDU could be sent to the SSP for display, as discussed in FIG. 8A.

FIG. 9A illustrates system operation using the stereoscopic smart phone (SSP). 901 illustrates the SSP. 902A illustrates a digital icon symbolizing an app, which would be installed and appear on the general display containing multiple apps 903 (including settings, clock, messages). The user could touch his/her finger 904A to the icon which would enable the SSP to receive commands for setting for the mode of operation of the stereoscopic cameras. These commands could be issued through but limited to: default settings; voice commands by the user into the smart phone via a microphone; antenna 905; via wire 906 into the data port 907; electronic message from the SHDU received at the smart phone. Note that a pull-down menu could appear on the smart phone display once the starting process has been initiated or by pull down menu on the SHDU.

FIG. 9B illustrates near real-time stereo mode at time N. At Time N, the user is enjoying a day at the beach and the stereoscopic cameras are pointed straight ahead at a small ship passing by. The smart phone display shows a split screen of left viewing perspective imagery 908 taken by the left camera and right viewing perspective imagery 909 taken by the right camera.

FIG. 9C illustrates system operation using the stereoscopic smart phone (SSP) with convergence mode. 901 illustrates the SSP. 902B illustrates a digital icon symbolizing the convergence option, which would be installed within the app. The user could touch his/her finger 904B to the convergence icon. The cameras will adjust according to the convergence point.

The user touches the display and the current mode of operation of the stereoscopic cameras is indicated by an icon 902B. A command "Converge Near" is issued and the mode of operation changes to convergence at short range The user can the read his/her book and see it in stereo on the SHDU. In some embodiments, eye tracking can be used to determine a location where in the user's environment a user is looking. Then, the stereoscopic cameras will adjust the convergence and zoom settings in order to optimize viewing of the location where the user is looking.

FIG. 9D illustrates convergence mode at time N+1. At a later time, Time N+1, the user wearing the SHDU decides to read a book using the SSP under convergence mode. The book is also shown on the smart phone display. Split screen is illustrated 908B and 909B for left and right eyes respectively. Note that in some embodiments, the stereo distance is adjusted so that it is different in FIG. 9D as compared to FIG. 9B. This could be done by using either the stereoscopic cameras on the front of the SSP or the stereoscopic cameras on the back of the SSP. In some embodiments, a novel stereoscopic camera setup with adjustable stereo distances is disclosed.

FIG. 10A illustrates of before application of automatic object recognition as displayed on the stereoscopic head display unit.

The purpose of these Figures is to illustrate of before and after application of automatic object recognition (AOR) as displayed on the SHDU. The context for this figure is that the wearer is taking a hike in the forest. The smart phone with stereoscopic cameras could be worn as a body camera, running continuously. The body camera is operating in a look forward mode scanning back and forth covering a hemispherical or near hemispherical field of regard. The SHDU could be operating in the mixed reality mode. FIG. 10A depicts the cluttered forest scene with trees, bush and grass and, some objects of possible interest which are difficult to distinguish among all the forest vegetation. The scene as it appears at Time 1 is shown on the SHDU 1001 using a left eye display 1002 and right eye display 1003. The user issues the command "Run AOR" and, in a very short time interval, FIG. 10B appears on the SHDU displays.

FIG. 10B illustrates after application of automatic object recognition as displayed on the stereoscopic head display unit. Again, the user in the forest enjoying the daytime hike. The smart phone is worn like a body camera and in the scanning mode (at least a 60 degree arc covering the path and 30 degrees to either side) alternating between looking straight ahead and looking down at close range. The SHDU is in the mixed reality mode an the AOR and AI are operating together. As circumstances would happen, there was a item of interest (e.g., snake which is dangerous) near the path. The AOR would detect and classify the snake and rapidly pass the information to the AI. The AI would assess the situation as 'danger close' and immediately provide feedback to the user (e.g., flash 'STOP, STOP, STOP' in big red letters on the SHDU displays). The SHDU speakers would sound the alarm and repeat STOP. There are literally numerous situations wherein the combination of AOR and AI would be beneficial to the user. FIG. 10B thus illustrates wherein the AOR has correctly classified the man and the deer in the scene. 1004A illustrates a man visible through the left see-through portion of the SHDU. Note that in some embodiments, an image from a left stereoscopic camera of a man can be displayed on the left eye display of the SHDU. 1004B illustrates a man visible through the right see-through portion of the SHDU. Note that in some embodiments, an image from a right stereoscopic camera of a man can be displayed on the right eye display of the SHDU. 1005A illustrates a deer visible through the see-through portion of the SHDU. Note that in some embodiments, an image from a left stereoscopic camera of a deer can be displayed on the left eye display of the SHDU. 1005B illustrates a deer visible through the see-through portion of the SHDU. Note that in some embodiments, an image from a right stereoscopic camera of a deer displayed on the right eye display of the SHDU. Note that in some embodiments, some items within the scene have been filtered (subtracted from the scene). This improves understanding of the items of interest. Note that in some embodiments, a novel augmented reality feature is to label an item within the field of view, such as the men and deer are labeled for easy user recognition.

FIG. 10C invokes another stereo camera unique technology. Specifically, since the cameras are of higher resolution than the SHDU displays, the pixels on the display are down sampled in order to get the full scene in the field of view (FOV) onto the SHDU displays. At the user command "Focus deer", the stereoscopic cameras change the FOV to the narrow field of view (NFOV). For the NFOV, the down sampling is discontinued and, in a very short time interval, the left image 1006A of the deer from the left stereoscopic camera is displayed in full resolution on left eye display and the right image 1006B of the deer from the right stereoscopic camera deer is displayed in full resolution on right eye display. These images are displayed at Time 1++.

At each of pre-planned FOVs the AOR is run and objects of potential interest are identified and displayed in the SHDU displays.

For example, consider this scenario as the walk progresses, it becomes necessary for the user to cross a road. A very quiet electric vehicle (EV) is approaching. The AOR recognizes the vehicle and passes it to the AI. AI self tasks the question 'is it safe for the user to cross the road'. The SHDU is equipped with a laser range fonder (LRF) which is used to determine range from the user to the EV and range rate of change of the of the EV (i.e., the AI problem is "how fast is the EV going?" and "when will the vehicle get to the user location?"). If the expected arrival time of the EV is such that the EV might intersect with the user, then the SHDUs would flash in large letters 'DANGER, DANGE, DANGER'. The speakers in the SHDU would sound a warning siren. This could be performed in a variety of scenarios.

FIG. 11A illustrates integration of image stabilization for a user in a scene where there is vibration.

The scene depicted in FIG. 11A is that of a user 1101 riding in a subway along with other passengers labeled 1104. The user 1101 is wearing a SHDU 1102 and holding a stereoscopic camera wherein the phone is linked into the internet. The user spots an article of interest and downloads the article. The subway environment is such that there is considerable vibration thereby, making reading difficult. The user decides to invoke stereoscopic image stabilization. Note that the user, in this case, could invoke either SHDU setting for either mixed reality (MR) wherein the user could read the article and simultaneously watch the ongoing activities in the subway car. Alternatively, the user could invoke the option on the SHDU for virtual reality (VR) and obscure to external scene and focus solely on the article of interest. Note that the user could easily change form the VR mode to the MR mode if there were announcements in the subway communication system.

FIG. 11B shows selection of points within the image to use for image stabilization. The SHDU 1105 displays wherein, for the stereoscopic image stabilization for left eye display has selected three words (1106, 1107 and 1108) within the displayed image (text in this example) as reference points to adjust left eye image frame display to sequential next left eye image frame display. Similarly, 109, 1110, and 1111 are reference points for the right eye display and are used to adjust right eye image frame display to sequential next right eye image frame display. This adjustment process from frame to frame would continue until the user proceeded to other parts of the article at which time the stereoscopic image stabilization process would select new reference points.

FIG. 11C illustrates illustrates selection of points within the scene to use for image stabilization. A user 1112 on a walk thru an area of interest which, in this case is an urban area. The user, 1112, is wearing a SHDU 1113 and has a smart stereoscopic camera 1114 in a body wear position to operate in the continuous mode operation of streaming stereoscopic imagery from the stereoscopic cameras. Within the area within which the user is walking there are structures including a first building 1115, a second building 1116 and a fountain 1117, each of which has distinctive features which could be used as reference points for stereoscopic image stabilization. Note that the user may choose to use the microphone on the SHDU to record observations during the walk thru the area of interest.

FIG. 11D illustrates stereoscopic image stabilization on the SHDU. FIG. 11D shows the SHDU 1118 wherein, for the stereoscopic image stabilization for left eye display has selected three key points within the area (1119, 1120 and 1121) as reference points to adjust left eye image frame display to sequential next left eye image frame display. Similarly, 1122, 1123, and 1124 are reference points for the right eye display and are used to adjust right eye image frame display to sequential next right eye image frame display. This adjustment process from frame to frame would continue until the user proceeded to other parts of the article at which time the stereoscopic image stabilization process would select new reference points. In some embodiments, for the left image displayed in the SHDU 1118, a first set of points is used for image stabilization and for the right image displayed in the SHDU 1118, the same first set of points is used for image stabilization. In other embodiments, for the left image displayed in the SHDU 1118, a first set of points is used for image stabilization and for the right image displayed in the SHDU, a second set of points is used for image stabilization wherein the first set of points are different from the second set of points.

FIG. 12A illustrates determining a stabilization point and field of view (FOV) for the left eye imagery and right eye imagery. Left eye imagery and right eye imagery at time=N and time=N+1 are shown. 1200 illustrates a point in the left eye imagery, which is used for image stabilization at time=N. 1200A illustrates the field of view (FOV) from the left eye imagery. 1200B illustrates a portion of the field of view (FOV) from the left eye imagery, which is the portion to be displayed to a user. Note that 1200B is a subset of 1200A, which is determined based on point 1200. In the preferred embodiment, 1200A is based on using the point 1200 as the center of 1200A. 1201 illustrates a point in the right eye imagery, which is used for image stabilization at time=N. 1201A illustrates the field of view (FOV) from the left eye imagery. 1201B illustrates a portion of the field of view (FOV) from the left eye imagery, which is the portion to be displayed to a user. Note that 1201B is a subset of 1201A, which is determined based on point 1201. In the preferred embodiment, 1201A is based on using the point 1201 as the center of 1201A. 1202 illustrates the point in the left eye imagery, which is used for image stabilization at time=N+1. 1202A illustrates the field of view (FOV) from the left eye imagery. 1202B illustrates a portion of the field of view (FOV) from the left eye imagery, which is the portion to be displayed to a user. Note that 1202B is a subset of 1202A, which is determined based on point 1202. In the preferred embodiment, 1202A is based on using the point 1202 as the center of 1202A. 1203 illustrates the point in the right eye imagery, which is used for image stabilization at time=N+1. 1203A illustrates the field of view (FOV) from the left eye imagery.

1203B illustrates a portion of the field of view (FOV) from the left eye imagery, which is the portion to be displayed to a user. Note that 1203B is a subset of 1203A, which is determined based on point 1203. In the preferred embodiment, 1203A is based on using the point 1203 as the center of 1203A. In some embodiments, a characteristic feature which can be easily distinguished in the image is used as a stabilizing point for both the left eye imagery and the right eye imagery. In some embodiments, the stabilizing point for the left eye imagery is different from the stabilizing point for the right eye imagery. In some embodiments, image stabilization is used for close range imagery, but not for longer range imagery. In some embodiments, a delay of less than 5 seconds is performed.

FIG. 12B illustrates displaying stabilized stereoscopic imagery on a SHDU. 1204 illustrates the stereoscopic head display unit (SHDU). The top image illustrates what is displayed in a SHDU at time=N+delay, which includes the portion of the field of view (FOV) from the left eye imagery 1200B for the left eye display and the portion of the field of view (FOV) from the right eye imagery 1201B for the right eye display. The bottom image illustrates what is displayed in a SHDU at time=N+delay, which includes the portion of the field of view (FOV) from the left eye imagery 1202B for the left eye display and the portion of the field of view (FOV) from the right eye imagery 1203B for the right eye display.

FIG. 13A illustrates the SSP with its stereoscopic cameras in a first position, which is wide. 1300A illustrates the SSP in a first configuration at time=N. 1301A illustrates a first camera of the SSP's stereoscopic camera system, which is located at a first position on the SSP. 1302A illustrates a second camera of the SSP's stereoscopic camera system, which is located at a second position on the SSP. Note that the first camera 1301A is separated from the second camera 1302A by a first stereo distance.

FIG. 13B illustrates the SSP with its stereoscopic cameras in a second position, which is wide. 1300B illustrates the SSP in a second configuration at time=N+1. Note that the second configuration is different from the first configuration. 1301B illustrates the first camera of the SSP's stereoscopic camera system, which is located at a third position on the SSP. 1302B illustrates the second camera of the SSP's stereoscopic camera system, which is located at a fourth position on the SSP. Note that the first camera 1301B is now separated from the second camera 1302B by a second stereo distance, which is different from the first stereo distance. Note that in this example, the second stereo distance is smaller than the first stereo distance.

FIG. 13C illustrates the SSP with its stereoscopic cameras in a third position, which is also narrow, but shifted in position as compared to FIG. 12B. 1300C illustrates the SSP in a third configuration at time=N+2. Note that the third configuration is different from the first configuration and also different from the second configuration. 1301C illustrates the first camera of the SSP's stereoscopic camera system, which is located at a fifth position on the SSP. 1302C illustrates the second camera of the SSP's stereoscopic camera system, which is located at a sixth position on the SSP. Note that the first camera 1301B is separated from the second camera 1302B by the second stereo distance, but the position of the cameras is shifted. This novel design improves tracking of small objects that move, such as a rolly polly. In this example, the cameras are shown to move along a line. This is called a camera bar design. In some embodiments, the cameras could move up, down, forward, back, left or right. In some embodiments, the cameras' orientations can also be adjusted in roll, pitch and yaw. In some embodiments, the movements of the cameras can be coordinated with convergence as shown in FIG. 2C. Thus, a novel aspect of this system is that the SSP's stereoscopic cameras can be reconfigured into different positions and orientations on the SSP. This reconfigurable design would allow depth at various distances and could achieve depth at ranges of <2 inches satisfactory. In some embodiments, a first set of lenses for the stereoscopic camera system could be used for a first stereo distance and a second set of lenses for the stereoscopic camera system could be used for a second stereo distance wherein the first set of lenses are nearer focus lenses than the second set of lenses and the first stereo distance is smaller than the second stereo distance.

FIG. 14 illustrates optimizing stereoscopic imaging. 1400 illustrates determining an object of interest. The preferred embodiment is to use automatic object recognition (AOR). Some embodiments comprise using eye tracking, as taught in U.S. patent application Ser. No. 16/997,830, ADVANCED HEAD DISPLAY UNIT FOR FIRE FIGHTERS, filed on Aug. 19, 2020. Some embodiments comprise wherein a user selects an object of interest via a graphical user interface or voice commands. 1401 illustrates determining the distance and angle from the stereoscopic cameras to the object of interest. The preferred embodiment is to use a laser range finder, as taught by U.S. Pat. No. 11,006,100, SMART GLASSES SYSTEM. Other distance measurement technologies are also possible. In some embodiments, the colors and brightness of the images are also determined. 1402 illustrates reconfiguring stereoscopic cameras based on the distance from the stereoscopic camera wherein reconfiguring the stereoscopic cameras comprises adjusting: changing the stereo separation of the left stereoscopic camera from the right stereoscopic camera; moving the left stereoscopic camera and the right stereoscopic camera; changing the convergence of the left stereoscopic camera and the right stereoscopic camera; changing the zoom setting of the left stereoscopic camera and the right stereoscopic camera; and, changing the ISO setting of the left stereoscopic camera and the right stereoscopic camera. Other adjustments include: adjusting the shutter speed; adjusting the focal length; adjusting the field of view; adjusting the detector position/orientation; adjusting the camera position/orientation; adjust the convergence angle; and adjusting a deformable mirror. In some embodiments, these adjustments are also based on the colors and brightness of the images. In some embodiments, a table for optimized stereoscopic camera settings is generated based on distance. This table can be referenced as a look up table. Once the distance and angle is determined, the camera settings can be looked up and automatically implemented. For X distance, stereo distance would be looked up and found to be Y. And the stereoscopic cameras would be set at a stereo distance of Y.

Figure 15:
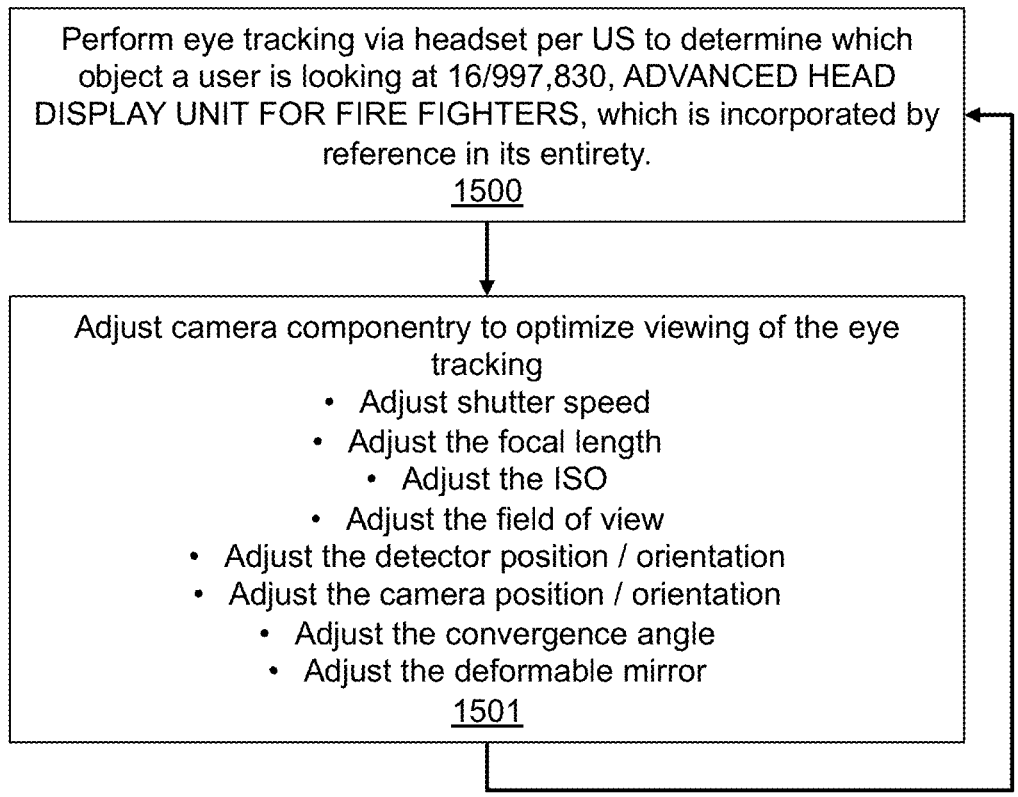
FIG. 15 illustrates adjusting stereoscopic camera componentry based on eye tracking parameters of a user.

FIG. 15 illustrates adjusting stereoscopic camera componentry based on eye tracking parameters of a user. 1500 illustrates performing eye tracking via headset per US to determine which object a user is looking at Ser. No. 16/997, 830, ADVANCED HEAD DISPLAY UNIT FOR FIRE FIGHTERS, which is incorporated by reference in its entirety. 1501 illustrates adjust camera componentry to optimize viewing of the eye tracking, which includes: adjusting the shutter speed; adjusting the focal length; adjusting the ISO; adjusting the field of view; adjusting the detector position/orientation; adjusting the camera position/orientation; adjust the convergence angle; and adjusting a deformable mirror. In some embodiments, eye tracking is used to adjust the camera componentry to optimize imaging using a single camera system. In some embodiments, eye tracking is used to adjust the camera componentry to optimize imaging using a stereoscopic camera system.

Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method of stereoscopic imaging comprising:
using a left camera and a right camera of a stereoscopic camera system image to perform initial stereoscopic imaging of an area
wherein said left camera has a location on said stereoscopic camera system,
wherein said right camera has a location on said stereoscopic camera system,
wherein said left camera's location and said right camera's location are separated by a first stereoscopic distance,
wherein said left camera has a first pointing direction,
wherein said right camera has a first pointing direction, and
wherein said left camera's first pointing direction is different from said right camera's first pointing direction, and
wherein said left camera's first pointing direction and said right camera's first pointing direction are towards a first convergence point;
changing said left camera's first pointing direction to a second pointing direction
wherein said left camera's second pointing direction is different than said left camera's first pointing direction,
wherein said left camera's second pointing direction points towards a second convergence point,
wherein said second convergence point is different from said first convergence point, and
wherein either said left camera's location on said stereoscopic camera changes based on said second convergence point or said left camera's zoom setting changes based on said second convergence point;
changing said right camera's first pointing direction to a second pointing direction
wherein said right camera's second pointing direction is different than said right camera's first pointing direction,
wherein said right camera's second pointing direction points towards said second convergence point,
wherein said left camera's second pointing direction is different from said right camera's second pointing direction, and
wherein either said right camera's location on said stereoscopic camera changes based on said second convergence point or said right camera's zoom setting changes based on said second convergence point; and
using said left camera and said right camera of said stereoscopic camera system to perform subsequent stereoscopic imaging of said area with said left camera's second pointing direction and said right camera's second pointing direction.

2. The method of claim 1 further comprising:
wherein said first convergence point is positioned such that a distance from said left camera's location to said first convergence point is not equal to a distance from said right camera's location to said first convergence point; and
wherein said left camera's zoom setting does not equal said right camera's zoom setting.

3. The method of claim 1 further comprising wherein said second convergence point is positioned such that a distance from said left camera's location to said second convergence point is equal to a distance from said right camera's location to said second convergence point.

4. The method of claim 1 further comprising:
wherein if said left camera's location changes to a new location and if said right camera's location changes to a new location, said left camera's new location and said right camera's new location are separated by a second stereoscopic distance; and
wherein said second stereoscopic distance is different from said first stereoscopic distance.

5. The method of claim 1 further comprising:
wherein a distance from said stereoscopic camera system to said first convergence point is smaller than a distance from said stereoscopic camera system to said second convergence point;
wherein said initial stereoscopic imaging has a first zoom setting;
wherein said subsequent stereoscopic imaging has a second zoom setting; and
wherein said second zoom setting has greater magnification than said first zoom setting.

6. The method of claim 1 further comprising:
wherein said left camera's first pointing direction is determined based on said left camera's orientation; and
wherein said right camera's first pointing direction is determined based on said right camera's orientation.

7. The method of claim 1 further comprising:
displaying left eye imagery and right eye imagery from said initial stereoscopic imaging of said area on a stereoscopic head display unit (SHDU); and
displaying left eye imagery and right eye imagery from said subsequent stereoscopic imaging of said area on said SHDU wherein said SHDU comprises a virtual reality display, an augmented reality display or a mixed reality display.

8. The method of claim 7 further comprising:
wherein said stereoscopic camera system is acquired on a smart phone;
wherein said first convergence point and second convergence point are determined based on object tracking in said area; and
wherein said SHDU and said smart phone communicate via a wired connection, a wireless connection via Bluetooth or a wireless connection via an Internet.

9. The method of claim 7 further comprising wherein automatic object recognition is performed on said left eye imagery and said right eye imagery from said initial stereoscopic imaging of said area on said SHDU.

10. The method of claim 9 further comprising wherein artificial intelligence is performed in conjunction with said automatic object recognition to alert a user regarding findings in said area.

11. The method of claim 7 further comprising wherein stereoscopic image stabilization is performed on said left eye imagery and said right eye imagery from said initial stereoscopic imaging of said area on said SHDU.

12. The method of claim 1 further comprising:
determining a spatial relationship between said stereoscopic camera system and an object of interest; and
reconfiguring said stereoscopic cameras based on said spatial relationship wherein reconfiguring said stereoscopic cameras comprises changing said stereoscopic distance to a subsequent stereoscopic distance wherein said subsequent stereoscopic distance is different than said stereoscopic distance.

13. The method of claim 1 further comprising:
wherein said subsequent stereoscopic imaging of said area is performed using a second stereoscopic distance; and
wherein said second stereoscopic distance is smaller than said first stereoscopic distance.

14. The method of claim 1 further comprising wherein said stereoscopic camera system is placed on a smart phone, a tablet or a laptop.

15. The method of claim 1 further comprising:
wherein a scene sensing device maps said area;
wherein tracking of an object in said area is performed;
wherein said first convergence point is determined based on said object's location in said area at a first time point and said second convergence point is determined based on said object's location in said area a first time point.

16. The method of claim 1 further comprising wherein said first convergence point and said second convergence point are determined based on eye tracking metrics of a user.

17. The method of claim 1 further comprising wherein said first convergence point and said second convergence point are determined based on an artificial intelligence algorithm.

18. The method of claim 1 further comprising wherein a sensor system of said stereoscopic camera system comprises a composite sensor array.

19. A stereoscopic head display unit (SHDU) comprising:
a head display unit with a left eye display and a right eye display wherein said SHDU is configured to:
receive initial stereoscopic imagery from a stereoscopic imaging system
wherein said initial stereoscopic imagery comprises initial left eye imagery and initial right eye imagery;
display said initial left eye imagery on said left eye display;
display said initial right eye imagery on said right eye display;
receive subsequent stereoscopic imagery from said stereoscopic imaging system wherein said subsequent stereoscopic imagery comprises subsequent left eye imagery and subsequent right eye imagery;
display said subsequent left eye imagery on said left eye display;
display said subsequent right eye imagery on said right eye display;
wherein said stereoscopic imaging system comprises a left camera and a right camera; and
wherein said stereoscopic camera system image is configured to:
use said left camera and said right camera of said stereoscopic camera system to perform said initial stereoscopic imaging of an area
wherein said left camera has a location on said stereoscopic camera system, wherein said right camera has a location on said stereoscopic camera system,
wherein said left camera's location and said right camera's location are separated by a first stereoscopic distance,
wherein said left camera has a first pointing direction,
wherein said right camera has a first pointing direction, and
wherein said left camera's first pointing direction is different from said right camera's first pointing direction, and
wherein said left camera's first pointing direction and said right camera's first pointing direction are towards a first convergence point;
change said left camera's first pointing direction to a second pointing direction
wherein said left camera's second pointing direction is different than said left camera's first pointing direction,
wherein said left camera's second pointing direction points towards a second convergence point, and
wherein said left camera's location on said stereoscopic camera changes based on said second convergence point;
change said right camera's first pointing direction to a second pointing direction
wherein said right camera's second pointing direction is different than said right camera's first pointing direction, and
wherein said right camera's second pointing direction points towards said second convergence point,
wherein said left camera's second pointing direction is different from said right camera's second pointing direction,
wherein said right camera's location on said stereoscopic camera setting changes based on said second convergence point,
wherein said left camera's location and said right camera's location are separated by a second stereoscopic distance, and
wherein said second stereoscopic distance is different from said first stereoscopic distance; and
use said left camera and said right camera of said stereoscopic camera system to perform said subsequent stereoscopic imaging of said area with said left camera's second pointing direction and said right camera's second pointing direction.

20. A stereoscopic smart phone comprising:
a smart phone; and
a stereoscopic imaging system operably connected to said smart phone comprising a left camera and a right camera wherein said stereoscopic camera system image is configured to:
perform initial stereoscopic imaging of an area
wherein said left camera has a location on said stereoscopic camera system,
wherein said right camera has a location on said stereoscopic camera system,
wherein said left camera's location and said right camera's location are separated by a stereoscopic distance, and
wherein said left camera has a first pointing direction,
wherein said right camera has a first pointing direction,
wherein said left camera's first pointing direction is different from said right camera's first pointing direction, and
wherein said left camera's first pointing direction and said right camera's first pointing direction are towards a first convergence point;
change said left camera's first pointing direction to a second pointing direction
wherein said left camera's second pointing direction is different than said left camera's first pointing direction,
wherein said left camera's second pointing direction points towards a second convergence point, and
wherein said left camera's zoom setting changes based on said second convergence point;
change said right camera's first pointing direction to a second pointing direction,
wherein said right camera's second pointing direction is different than said right camera's first pointing direction,
wherein said right camera's second pointing direction points towards said second convergence point,
wherein said left camera's second pointing direction is different from said right camera's second pointing direction, and
wherein said right camera's zoom setting changes based on said second convergence point; and
use said left camera and said right camera of said stereoscopic camera system to perform subsequent stereoscopic imaging of said area with said left camera's second pointing direction and said right camera's second pointing direction.

* * * * *